(12) United States Patent
Davisson

(10) Patent No.: US 7,045,674 B2
(45) Date of Patent: May 16, 2006

(54) ANIMAL MODEL FOR PREECLAMPSIA

(75) Inventor: Robin L. Davisson, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 10/666,980

(22) Filed: Sep. 19, 2003

(65) Prior Publication Data

US 2004/0133929 A1    Jul. 8, 2004

Related U.S. Application Data

(60) Provisional application No. 60/411,992, filed on Sep. 19, 2002.

(51) Int. Cl.
*G01N 33/00* (2006.01)

(52) U.S. Cl. ......................................................... 800/3

(58) Field of Classification Search ................. 424/9.1, 424/9.2; 800/3
See application file for complete search history.

(56) References Cited

OTHER PUBLICATIONS

Takimoto "Hypertension induced in pregnant mice by placental renin and maternal angeiotensinogen," Science 274(5289): 995-998, 1996.*

Makino et al. "Adrenomedullin attenuates the hypertension in hypertensive pregnant rats induced by Ng-nitro-L-arginine methyl ester," European Journal of Pharmacology 371: 159-167, 1999.*

Douglas BH "The rat as a model for preeclampsia." Perspect Nephrol Hypertens 5:411-419, 1976 (Abstract only).*

Crossey et al. "Altered placental development and intrauterine growth restriction in IGF binding protein-1 transgenic mice." Journal of Clinical Investigation 110(3): 411-418, 2002.*

Bohlender et al. "Rats transgenic for human renin and human angiotensinogen as a model for gestational hypertension." 11(11): 2056-2061, 2000.*

Hammer et al. "Spontaneous inflammatory disease in transgenic rats expressing HLA-B27 and human B2m: an animal model of HLA-B27-associated human disorders." Cell 63: 1099-1112, 1990.*

Cameron et al. "Recent advances in transgenic technology." Molecular Biotechnology 7:253-265, 1997.*

* cited by examiner

*Primary Examiner*—Michael Wilson
(74) *Attorney, Agent, or Firm*—McKee, Voorhees & Sease, P.L.C.

(57) ABSTRACT

The invention provides an animal model for preeclampsia that allows candidate compounds to be screened for their ability to treat preeclampsia.

5 Claims, 5 Drawing Sheets

SEQUENCE LISTING

```
<160> NUMBER OF SEQ ID NOS: 16

<210> SEQ ID NO 1
<211> LENGTH: 24
<212> TYPE: DNA
<213> ORGANISM: Mus musculus

<400> SEQUENCE: 1
gaaatgcagc tgactttgaa tctt                                              24
```

<210> SEQ ID NO 2
<211> LENGTH: 18
<212> TYPE: DNA
<213> ORGANISM: Mus musculus

<400> SEQUENCE: 2
ggcttgacac cagcagca                                          18

<210> SEQ ID NO 3
<211> LENGTH: 22
<212> TYPE: DNA
<213> ORGANISM: Mus musculus

<400> SEQUENCE: 3
tggacctatg gcctgatgtt aa                                     22

<210> SEQ ID NO 4
<211> LENGTH: 21
<212> TYPE: DNA
<213> ORGANISM: Mus musculus

<400> SEQUENCE: 4
ttgctcgctg ttttctggag t                                      21

<210> SEQ ID NO 5
<211> LENGTH: 20
<212> TYPE: DNA
<213> ORGANISM: Mus musculus

<400> SEQUENCE: 5
gggagcttgt tgacacgctt                                        20

<210> SEQ ID NO 6
<211> LENGTH: 17
<212> TYPE: DNA
<213> ORGANISM: Mus musculus

<400> SEQUENCE: 6
cggcttgaag gcctgct                                           17

<210> SEQ ID NO 7
<211> LENGTH: 24
<212> TYPE: DNA
<213> ORGANISM: Mus musculus

<400> SEQUENCE: 7
ggctcacaca ctattcagct cttc                                   24

<210> SEQ ID NO 8
<211> LENGTH: 18
<212> TYPE: DNA
<213> ORGANISM: Mus musculus

<400> SEQUENCE: 8
cgtccagagg gctttccc                                          18

<210> SEQ ID NO 9
<211> LENGTH: 18
<212> TYPE: DNA
<213> ORGANISM: Mus musculus

-continued

```
<400> SEQUENCE: 9
tgaagcatct ccccggaa                                               18

<210> SEQ ID NO 10
<211> LENGTH: 22
<212> TYPE: DNA
<213> ORGANISM: Mus musculus

<400> SEQUENCE: 10
gttggatcaa agaagggagc at                                          22

<210> SEQ ID NO 11
<211> LENGTH: 21
<212> TYPE: DNA
<213> ORGANISM: Mus musculus

<400> SEQUENCE: 11
catcttcaag ccgtcctgtg t                                           21

<210> SEQ ID NO 12
<211> LENGTH: 21
<212> TYPE: DNA
<213> ORGANISM: Mus musculus

<400> SEQUENCE: 12
cagggcttca tcgttacagc a                                           21

<210> SEQ ID NO 13
<211> LENGTH: 20
<212> TYPE: DNA
<213> ORGANISM: Mus musculus

<400> SEQUENCE: 13
cctcattgtc cttggctgga                                             20

<210> SEQ ID NO 14
<211> LENGTH: 24
<212> TYPE: DNA
<213> ORGANISM: Mus musculus

<400> SEQUENCE: 14
ttataatgaa ggcttgctgc actt                                        24

<210> SEQ ID NO 15
<211> LENGTH: 22
<212> TYPE: DNA
<213> ORGANISM: Mus musculus

<400> SEQUENCE: 15
cattgaacag tcgggcgagt at                                          22

<210> SEQ ID NO 16
<211> LENGTH: 17
<212> TYPE: DNA
<213> ORGANISM: Mus musculus

<400> SEQUENCE: 16
ccccggtgcg aagttct                                                17
```

ANIMAL MODEL FOR PREECLAMPSIA

CROSS-REFERENCE TO RELATED APPLICATIONS

This application claims priority to U.S. Provisional Application Ser. No. 60/411,992 filed Sep. 19, 2002, which is herein incorporated by reference in its entirety.

BACKGROUND OF THE INVENTION

This invention relates generally to an animal model for preeclampsia that mimics the pathophysiology and etiology of the disease in humans.

Preeclampsia, the most prevalent hypertensive disorder of pregnancy, is defined by the triad of hypertension, proteinuria, and edema. It is thought to impact 6–10% of pregnancies and is the leading cause of maternal mortality in Western countries. Great Britain Department of Health, WHY MOTHERS DIE: REPORT ON CONFIDENTIAL ENQUIRIES INTO MATERNAL DEATHS IN THE UNITED KINGDOM 1994–1996. London; TSO (1998). A distinguishing feature of the disorder is its complete resolution following delivery of the fetus and placenta—the only known effective means to avoid cataclysmic progression to overt eclampsia. The necessity for urgent preterm delivery, along with progressive intrauterine growth restriction implicate preeclampisa as a leading cause of perinatal morbidity and mortality. National High Blood Pressure Education Program Working Group Report on High Blood Pressure in Pregnancy, *Am. J. Obstet. Gynecol.* 163:1691–1712 (1990). Hospitalization, strict bed rest, magnesium sulfate administration to prevent convulsions, and prompt delivery are the current standard of therapy for preeclampsia.

Despite its prevalence the exact cause of preeclampsia remains unclear. Current postulated theories include a primary causative role for the placenta, poor placental perfusion resulting in hypoxia and increased oxidative stress, Roberts et al. Lancet 354:788–789 (1999), an exaggerated activation of the maternal immune response, Chun et al., Obstet Gynaecol Br Commonw 71:180–184 (1964), and maternal predisposition due to underlying disorders associated with microvascular disease. The contribution of the placenta is evident from the findings that preeclampsia can develop in pregnancies without a fetus i.e., hydatidiform mole, (Chun et al., Obstet Gynaecol Br Commonw 71:180–184 (1964)), in pregnancies outside the uterus, (Piering et al., Am J Kid Dis 21:310–313 (1993)), and perhaps more importantly delivery, which removes this causative organ results in complete remission of the symptoms associated with preeclampsia. The link between reduced placental perfusion and the eventual manifestations of hypertension and renal dysfunction appears to be the release of a damaging factor(s) from the placenta that leads to widespread dysfunction of the maternal vascular endothelium. Alexander et al., News Phys Sci 16:282–286 (2001); Roberts et al., Am. J. Obstet. Gynecol. 161:1200–1204 (1989). Other studies have suggested a primary maternal vascular disorder with reduced organ perfusion secondary to vasospasm and activation of the coagulation cascade. Roberts et al., Am J Hypertens 4:700–708 (1991).

Timely expansion of the placental vasculature at the feto-maternal interface with appropriate perfusion appears be critical to the normal development and survival of the fetus. In the hemochorial human placenta the maternal blood perfuses a space lined by syncytiotrophoblasts that form the outer layer of the floating chorionic villi. The underlying stem cell cytotrophoblasts also differentiate into extravillus cells that display an invasive phenotype as they migrate along the cell column into the endometrium, inner-third of the myometrium and towards the spiral arteries. The replacement of the laminar smooth muscle of these maternal spiral arteries by the invading cytotrophoblasts results in marked dilatation of the arteries and increases blood supply to the expanding placenta. Most of these physiological changes are completed in the first half of gestation, although clinical manifestations of any dysregulation are usually seen later in pregnancy, as with preeclampsia. Recent data obtained from human placental biopsies have focused attention on abnormal cytotrophoblast-decidual interactions as a central culprit in the development of preeclampsia. Brosens et al., Obstet Gynecol Annu, 1:177–191 (1972); Zhou et al., J Clin Invest 99:2152–2164 (1997); Caniggia et al., J Clin Invest 103: 1641–1650(1999). These studies have demonstrated an incomplete invasion of trophoblasts into the uterus and its vasculature (Brosens et al., Obstet Gynecol Annu 1:177–191 (1972)), abnormalities in cytotrophoblast differentiation from an epithelial to endothelial phenotype (Zhou et al., J Clin Invest 99:2152–2164 (1997); Caniggia et al., J Clin Invest 103:1641–1650 (1999)), excess proliferation of immature intermediate trophoblasts (Redline et al., Hum Pathol 26:594–601 (1995)), and reduced expression of genes regulating angiogenesis such as vascular endothelial growth factor (VEGF)-A and its receptor VEGFR-1 (Zhou et al., Am J Pathol 160:1405–1423 (2002)). Although the primary trigger for the above abnormalities remains elusive, these impaired changes can result in decreased flow of oxygenated blood to the feto-placental unit, which in turn can contribute to the compromised fetal growth and low birth-weights observed in pregnancies complicated with severe preeclampsia. Alexander et al., News Phys Sci 16:282–286 (2001).

The preeclampsia/eclampsia syndrome was described by ancient civilizations. Despite considerable research effort to date, we still understand very little about its etiology and pathophysiology, which are complex and multifactorial. Morgan et al., *Sem. Perinatol.* 23:14–23 (1999). Clinical research is difficult due to the logistics of testing hypotheses related to pathogenesis or treatment in an urgent, high risk setting. Development of an animal model that fully recapitulates this complex hypertensive disorder would help broaden scientists' understanding of this disorder, and would hold great potential for design and implementation of effective prevention and treatment. Podjarny et al., *Sem. Perinatol.* 23:2–12 (1999).

Women with elevated baseline blood pressure prior to pregnancy have an increased risk for developing preeclampsia. Reiter et al., *Am. J. Kid. Dis.* 24:883–7 (1994). Understanding the complex mechanisms in the pathogenesis of preeclampsia is limited due to the difficulties in performing studies in pregnant women, and in part due to the lack of an animal model that fully recapitulates the disease. Many attempts have been made to generate animal models of preeclampsia, including uteroplacental ischemia (Losonczy et al., *Hypertension in Preg.* 12:475–85 (1993); Clark et al., *Am. J. Physiol.* 242:H297–H301 (1982)), chronic nitric oxide synthase inhibition (Yallampalli et al., *Am. J. Obstet. Gynecol.* 169:1316–20 (1993)), adriamycin nephropathy (O'Donnell et al., *J. Lab. Clin. Med.* 106:62–7 (1985)), and transgenic expression of human renin-angiotensin system genes (Takimoto et al., *Science* 274:995–8 (1996)). Each has been important for understanding certain aspects of the disease, although none recapitulate the full syndrome. Podjarny et al., *Sem. Perinatol.* 23:2–12 (1999). In most of these models, hypertension does not resolve upon delivery, and pathophysiological changes are observed both in pregnant and non-pregnant animals. Podjarny et al., *Sem. Perinatol.* 23:2–12 (1999). In view of the foregoing, it would be desirable to generate an animal model that fully recapitulates preeclampsia.

BRIEF SUMMARY OF THE INVENTION

A genetically borderline hypertensive mouse strain derived from the well-known hypertensive inbred strain BPH/2 was reported by Schlager and colleagues some years ago. Schlager et al., *FASEB J.* 3:A1315 (1989); Lester, J. W., SURVEY OF SELECTED PHYSIOLOGICAL PROPERTIES OF INBRED HYPERTENSIVE AND HYPOTENSIVE MICE," MA Thesis, Genetics Program, University of Kansas (1989); Schiager, "Genetic hypertension in mice," in HANDBOOK OF HYPERTENSION, pp. 158–72, Ganten et al., eds., Elsevier, Amsterdam, Netherlands (1994). BPH/5 is an inbred subline generated from brother-sister matings of fully inbred BPH/2 mice over many generations. Schlager, "Genetic hypertension in mice," in HANDBOOK OF HYPERTENSION, pp. 158–72, Ganten et al., eds., Elsevier, Amsterdam, Netherlands (1994). The inventors have discovered that, upon induction of pregnancy in BPH/5 female mice, the mice surprisingly exhibit symptoms that are identical with those of human preeclampsia. Specifically, Applicants have discovered that the BPH/5 strain exhibited mildly elevated pre-pregnancy blood pressure levels, spontaneously develops late-gestational hypertension, proteinuria, renal glomerulosclerosis and endothelial dysfunction. BPH/5 mice also exhibited reduced fetal weights and smaller litter sizes due to fetal demise in mid and late gestation suggesting a post-implantation phenomenon. Longitudinal ultrasound studies during pregnancy in these mice documented fetal demise prior to the onset of hypertension and proteinuria.

The present invention provides a method for screening for compounds useful for the treatment of preeclampsia comprising inducing preeclampsia in an animal, administering a test compound to the animal, and monitoring the animal for amelioration or elimination of preeclampsia. If, upon administration of the test compound, preeclampsia in the animal is ameliorated or eliminated, it is likely that the test compound is useful for the treatment of preeclampsia.

The present invention further provides a method for screening for compounds useful for the treatment of preeclampsia comprising mating a female BPH/5 mouse with a male mouse such that the female BPH/5 mouse becomes pregnant, administering a test compound to the pregnant BPH/5 mouse, and monitoring the pregnant BPH/5 mouse for the amelioration or elimination of preeclampsia. If, upon administration of the test compound, preeclampsia is ameliorated or eliminated, it is likely that the test compound is useful for the treatment of preeclampsia. The present invention also comprises a method of producing an animal that exhibits symptoms of preeclampsia comprising inducing preeclampsia in an animal; evaluating the presence pathological features characterized by placental morphological abnormalities, downregulation of genes associated with placental angiogenesis, and a decrease in uterine blood flow, whereby these features is indicative of the animal having preeclampsia relative to a control animal.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

Figure 1:
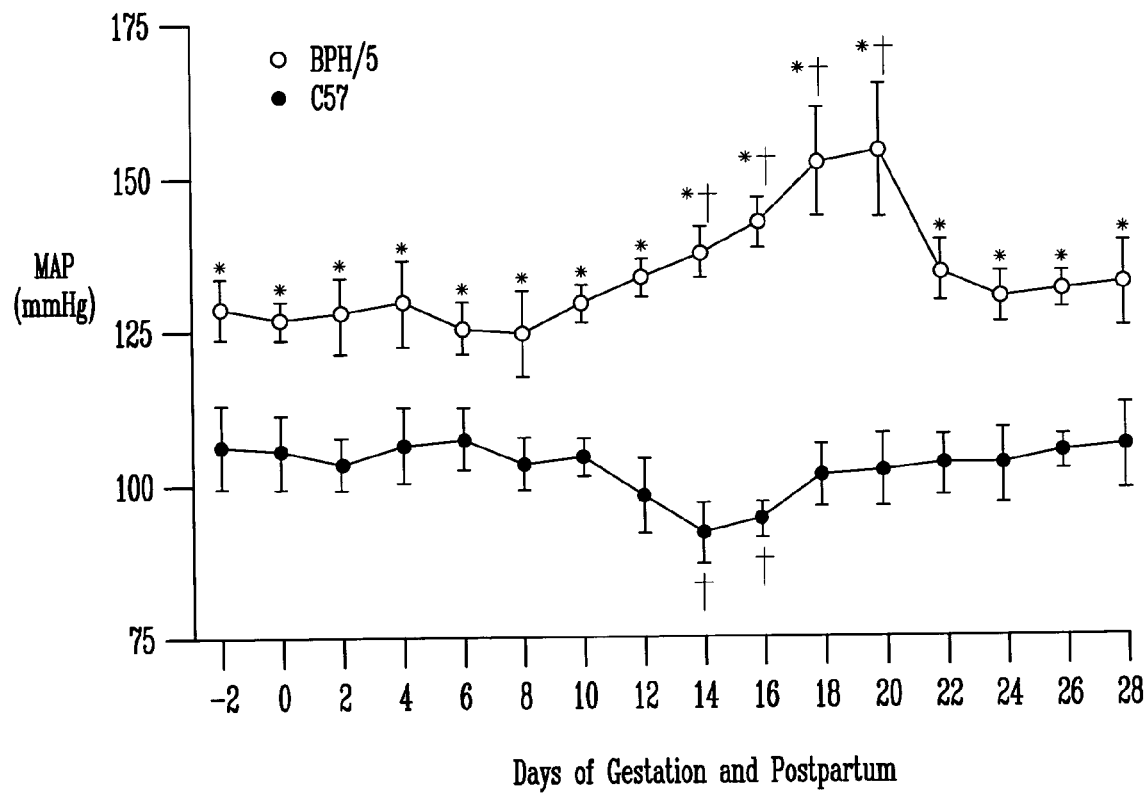
FIG. 1

BPH/5 develops gestational hypertension that resolves after delivery. Summary of mean arterial pressure (MAP) recorded longitudinally by radiotelemetry before, during and after pregnancy in BPH/5 (n=8) and C57BL/6 mice (n=7). Delivery was on day 20–21 (arrow), and day 0 corresponds to vaginal plug detection. Data are expressed as mean±SEM. *, $p<0.05$ vs. C57; ? $p<0.05$ vs. prepregnancy (day-2).

FIG. 2

BPH/5 exhibit proteinuria during late gestation. Summary of 24 hr urinary protein levels in BPH/5 and C57 mice that are either not pregnant (BPH/5, n=4; C57, n=5), at middle (BPH/5, n=4; C57, n=4) or at late gestation (BPH/5, n=5; C57, n=6). Mice were placed in metabolic cages and 24 hour urine samples were collected over 2 days. Data are expressed as mean±SEM. *, $p<0.05$ vs. C57; ? $p<0.01$ vs. non-pregnant.

FIG. 3

Glomerulosclerosis is observed during the last trimester of pregnancy in BPH/5. Representative photomicrographs of PAS-stained kidney sections from a non-pregnant C57 mouse (A) and BPH/5 mice that are non-pregnant (B), at day 15 (C) or day 19 (D, E) gestation. Magnification bar is 50 μm.

FIG 4

BPH/5 deliver small litters of low birth weight pups. Summary of litter sizes (Panel A, BPH/5, n=14; C57, n=15 litters) and neonatal birth weights (Panel B, BPH/5, n=34; C57, n=56 pups). Data are expressed as mean±SEM. * $p<0.05$ vs. C57.

FIG. 5

Fetal demise is the cause of reduced litter sizes in BPH/5. Panel A: Number of viable fetuses at early (BPH/5, n=8; C57, n=7), middle (BPH/5, n=5; C57, n=6) or late gestation (BPH/5, n=8; C57, n=9) as determined at necropsy. Data are expressed as mean±SEM. * $p<0.05$ vs. C57; ? $p<0.01$ vs. early gestation. Panel B: Representative cross-sectional fetal ultrasonogram in the plane of fetal hearts in a BPH/5 mouse on gestational day 12. An empty fetal sac (1) and two live fetuses (2 and 3) can be seen. Pulse-wave Doppler profiles of umbilical blood flow in fetuses 2 and 3 are shown. Upward deflection on Doppler tracings indicates umbilical artery flow, which is phasic, whereas the more continuous negative deflection arises from umbilical vein.

FIG. 6

Resistance arteries from pregnant BPH/5 mice have impaired endothelium-dependent relaxation. In vitro mesenteric arteries (~100 μm internal diameter) from late gestational (BPH/5, n=5, C57, n=5) or non-pregnant (BPH/5, n=9, C57, n=8) mice constricted with $10^{-7}$ M phenylephrine and relaxed with incremental doses of the endothelium-dependent vasodilator acetylcholine. Data are expressed as mean±SEM. * $p<0.05$ vs. all other groups; ? $p<0.05$ vs. BPH/5 pregnant.

DETAILED DESCRIPTION OF THE INVENTION

The present invention provides a method for screening for compounds useful for the treatment of preeclampsia comprising inducing preeclampsia in an animal, administering a test compound to the animal, and monitoring the animal for amelioration or elimination of preeclampsia. If, upon administration of the test compound, preeclampsia in the animal is ameliorated or eliminated, it is likely that the test compound is useful for the treatment of preeclampsia.

The present invention further provides a method for screening for compounds useful for the treatment of preeclampsia comprising mating a female BPH/5 mouse with a male mouse such that the female BPH/5 mouse becomes pregnant, administering a test compound to the pregnant BPH/5 mouse, and monitoring the pregnant BPH/5 mouse for the amelioration or elimination of preeclampsia. If, upon administration of the test compound, preeclampsia is ameliorated or eliminated, it is likely that the test compound is useful for the treatment of preeclampsia.

The present invention also comprises a method of producing an animal that exhibits symptoms of preeclampsia comprising inducing preeclampsia in an animal; evaluating the presence pathological features characterized by placental morphological abnormalities, downregulation of genes associated with placental angiogenesis, and a decrease in uterine blood flow, whereby these features is indicative of the animal having preeclampsia relative to a control animal.

Definitions

As used herein, the term "preeclampsia" includes a hypertensive, multi-system disorder of pregnant females, characterized by hypertension, proteinuria, edema, body-wide endothelial cell dysfunction, and placental maladaptation.

As used herein, the term "administering" is intended to refer to orally, parenterally, topically, rectally, bucally, nasally, or vaginally delivering a compound to an animal. The term "parenteral" as used herein includes subcutaneous, intracutaneous, intravenous, intramuscular, intra-articular, intrasynovial, intrasternal, intrathecal, intralesional and intracranial injection or infusion techniques.

As used herein, the term "animal" is intended to refer to humans and other vertebrate animals, including poultry, fish, cattle, swine, goats, lambs, dogs, cats, rodents, mice, rabbits, birds, deer, non-human primates, and others.

As used herein, the term "inducing preeclampsia" is intended to refer to the creation, in an animal, of a condition characterized by hypertension, proteinuria, edema, and body-wide endothelial cell dysfunction, and placental maladaptation. Preeclampsia can be induced by any method known in the art or developed in the future and does not necessarily require the presence of a fetus.

As used herein, the term "test compound" is intended to refer to a compound whose efficacy for treating a condition or disease, such as preeclampsia, in an animal can be evaluated. Possible test compounds in the present invention include, for example, magnesium sulfate, corticosteroids such as dexamethasone and betamethasone, anti-hypertensive drugs such as methyldopa, hydralazine, dihydralazine, calcium channel blockers (CCBs), angiotensin converting enzyme (ACE) inhibitors, diuretics, vasodilators, angiotensin II receptor blockers (ARBs), α- and β-andrenergic blockers, and statins.

Suitable CCBs include diltiazem, nifedipine, nitrendipine, nimodipine, niludipine, niguldipine, nicardipine, nisoldipine, amlodipine, felodipine, isradipine, ryosidine, verapamil, gallopamil and tiapamil.

Suitable ACE inhibitors include alacepril, benazepril, benazeprilat, captopril, ceronapril, cilazapril, delapril, enalapril, enalaprilat, fosinopril, imidapril, lisinopril, moveltopril, perindopril, quinapril, ramipril, spirapril, temocapril, and trandolapril.

Suitable diuretics include carbonic anhydrase inhibitors such as diclorphenamide; loop diuretics such as bumetanide, torsemide, ethacrynic acid and furosemide; potassium-sparing diuretics such as spironolactone, triamterene and amiloride; and thiazides such as hydroflumethiazide, chlorothiazide, hydrochlorothiazide, methychlothiazide, metolazone and chlorthalidone.

Suitable vasodilators include nitroglycerin and isosorbide mono- and di-nitrate.

Suitable β andrenergic blockers include propranolol, bisoprolol, metoprolol, atenolol, and labetalol.

Suitable statins include atorvastatin, cerivastatin, fluvastatin, lovastatin, itavastatin, pravastatin, and simvastatin.

As used herein, the term "monitoring," in reference to monitoring an animal for amelioration or elimination of a disorder following administration to the animal of a compound, is intended to refer to the testing of an animal for any change in the animal's physical condition. For example, preeclampsia is characterized, in part, by hypertension. It is well known that hypertension can be monitored through blood pressure determination. Thus, prior to administration of a compound to the animal, the animal's blood pressure can be taken by any suitable technique. Then, following administration of the compound, the animal's blood pressure can be taken in the same manner.

As used herein, the term "amelioration" is intended to refer to the reduction of one or more symptoms of a disorder, condition, or disease, for example preeclampsia.

As used herein, the term "elimination" is intended to refer to the elimination of all symptoms of a particular disorder, condition, or disease, for example preeclampsia. As used herein, the term "BPH/5 mouse" is intended to refer to an inbred subline generated from brother-sister matings of fully inbred BPH/2 mice over many generations, or any other mouse, derived from this line or not, which exhibits symptoms of preeclampsia when the female is impregnated, as shown by the methods and teachings herein. See, e.g., Schlager, "Genetic hypertension in mice," in HANDBOOK OF HYPERTENSION, pp. 158–72, Ganten et al., eds., Elsevier, Amsterdam, Netherlands (1994). As used herein, the term "BPH/2 mouse" is intended to refer to the product of a genetic selection for high blood pressure that was initiated in 1966 from a base population derived from an eight-way cross among LP/J, SJL/J, BALB/cJ, C57BL/J, 129/J, CBA/J, RF/J, and BDP/J, wherein inbreeding was avoided until F23, when several inbred substrains were initiated. BPH/2 mice exhibit high systolic blood pressure, shortened life span, low norephinephrine content in whole brain, larger relative heart and kidney weight, fewer glomeruli in the kidney, and larger 24-hour urinary volume.

This invention also provides molecular and immunohistochemical or immunopathological profiles in the mouse that are analogous to human preeclampsia. Therefore, this mouse model bears a close resemblance to the clinical disorder preeclampsia. Using this in vivo model, one can screen and evaluate various potential therapies or other modalities for their effectiveness in treating or alleviating preeclampsia, and evaluate any potential prophylactics. Since the model is an in vivo system it replicates, or is analogous to, the human clinical condition and provides clinical responses. For screening assays that use whole animals, a candidate agent or treatment is administered to the subject animals. Typically, a group of animals is used as a negative, untreated or placebo-treated control, and a test group is treated with the candidate therapy. Generally a plurality of assays are run in parallel with different agent dose levels to obtain a differential response to the various dosages. The dosages and routes of administration are determined by the specific compound or treatment to be tested, and will depend on the specific formulation, stability of the candidate agent, response of the animal, etc.

The analysis may be directed towards determining effectiveness in prevention of disease induction, where the treatment is administered before induction of the disease, i.e., prior to creation of a condition characterized by hypertension, proteinuria, edema, and body-wide endothelial cell dysfunction, and placental maladaptation. Alternatively, the analysis is directed toward ameliorating or eliminating this condition, and the treatment is administered after initial onset of the disease. Frequently, treatment effective for prevention is also effective in ameliorating or eliminating the disease.

In either case, after a period of time sufficient for the development or amelioration of the disease, the animals are assessed for impact of the treatment, by visual, histological, immunohistological, and other assays suitable for determining effectiveness of the treatment, all of which are known to those of ordinary skill in the art.

The model can further be utilized to identify nucleic acid sequences, i.e., genes, and/or amino acid sequences, i.e., proteins, that are associated with preeclampsia and its development, especially those that up- or down-regulate the disease.

In addition to these uses, the mouse model can act as a surrogate patient to evaluate the impact of a selected drug on preeclampsia before actual administration to the patient having the disease, and further, can aid in the prognosis of a patient. The model may also be used to identify or create other animal models based upon the BPH/5 phenotype observed here, including but no limited to the BPH/5 genotype, and the like.

This application refers to several scientific or patent publications to describe the state of the art to which the invention pertains. Each of these publications is incorporated by reference herein, in its entirety.

The following examples are for illustration only and are not intended to limit the invention in any way.

EXAMPLE 1

Animals and Husbandry

Experiments were performed in female (19–24 g) C57BL/6 (C57) or BPH/5 mice (kind gift of G. Schlager, University of Kansas), an inbred subline derived from >20 generations of brother-sister matings of the inbred spontaneously hypertensive strain BPH/2. Schlager et al., *FASEB J.* 3:A1315 (1989); Lester, J. W., SURVEY OF SELECTED PHYSIOLOGICAL PROPERTIES OF INBRED HYPERTENSIVE AND HYPOTENSIVE MICE," MA Thesis, Genetics Program, University of Kansas (1989); Schlager, "Genetic hypertension in mice," in HANDBOOK OF HYPERTENSION, pp. 158–72, Ganten et al., eds., Elsevier, Amsterdam, Netherlands (1994). BPH/5 exhibit baseline blood pressures that are significantly lower than BPH/2 but elevated above control. Schlager et al., *FASEB J.* 3:A1315 (1989); Lester, J. W., SURVEY OF SELECTED PHYSIOLOGICAL PROPERTIES OF INBRED HYPERTENSIVE AND HYPOTENSIVE MICE," MA Thesis, Genetics Program, University of Kansas (1989); Butz et al., *Physiol. Genomics* 5:89–97 (2001). Mice were housed in standard propylene cages placed in a temperature- and humidity-controlled facility, were maintained in a 12:12-hour light-dark cycle, and were fed standard mouse chow with water available ad libitum. Timed matings were carried out by strain-matched pairing of males and females overnight. Females were checked the next morning for the presence of a vaginal plug by gentle probing of the vaginal orifice with a blunt tapered glass rod. Butz et al., *Physiol. Genomics* 5:89–97 (2001). The day of plug detection was designated day 0 of pregnancy, at which time males were removed from the cage for the duration of pregnancy. Mice were weighed three times weekly to confirm pregnancy. Gestational stages are defined as follows: early, days 7–9; middle, days 11–14; late, days 16–20. Care of the mice met or exceeded standards set forth by the NATIONAL INSTITUTES OF HEALTH GUIDE FOR THE CARE AND USE OF LABORATORY ANIMALS. All procedures were approved by the University Animal Care and Use Committee at The University of Iowa.

Longitudinal Measurement of Blood Pressure Throughout Pregnancy Using Radiotelemetry Non-pregnant female BPH/5 (n=8) and C57 (n=9) mice underwent thoracic aortic implantation of radiotelemeters (Data Sciences International, St. Paul, Minn.) as described. Butz et al., *Physiol. Genomics* 5:89–97 (2001). Briefly, mice were anesthetized (ketamine, 90 mg/kg, acepromazine, 1.8 mg/kg, ip), a ventral midline neck incision was made, and the left common carotid artery was isolated, retracted (7-O silk), and a tiny incision was made. The pressure-sensing catheter was carefully inserted into the left carotid artery using vessel cannulation forceps and advanced 10 mm so that the tip resided just inside the thoracic aorta. The catheter was secured by ligatures and the transmitter body was tunneled subcutaneously to a small pouch along the right ventral flank. The neck incision was closed with 6-O silk and mice were kept warm until fully recovered from anesthesia. Following 7 days recovery in home cages (placed atop telemetry receivers), telemeters were magnetically activated and baseline mean arterial pressure (MAP) was recorded continuously for 5 days (sampling every 5 minutes for 10 second intervals). On day 13 post-surgery, telemeters were switched off and strain-matched breeding was carried out (see above). Upon detection of a vaginal plug, telemeters were re-activated and MAP was recorded continuously throughout pregnancy (20–21 days), and for an additional 1 wk postpartum. Data were collected on-line and stored using the Dataquest ART data acquisition system (Data Sciences International) as described. Butz et al., *Physiol. Genomics* 5:89–97 (2001).

Urinary Protein Measurements and Renal Histopathology

In separate timed mating experiments, BPH/5 and C57 mice without radiotelemeters were placed in individual metabolic cages with free access to food and water, and 24 hr urine samples were collected over 2 days. Three separate cohorts of each strain were studied. Mice were either not pregnant (BPH5 n=4; C57 n=5), middle gestational (BPH5 n=4, C57 n=4) or late gestational (BPH5 n=5, C57 n=6). Body mass (g) on entry and removal from the cage was recorded. Urine was frozen at −20° C. until being analyzed for total protein content using a protein assay kit (Bio-Rad) following manufacturer's instructions. Takimoto et al., *Science* 274:995–8 (1996). Immediately following urine collection, a subset of these mice were sacrificed by $CO_2$ asphyxiation and the kidneys removed and fixed in 10% neutral-buffered formalin. Tissue was embedded in paraffin, sectioned (4 µm saggital), and stained with periodic acid Schiff (PAS) for histopathological analysis. Kidneys from a minimum of two different mice from each strain and gestational stage were examined.

Analysis of Pregnancy Outcomes

Numbers of live pups born and neonatal body mass (g) were recorded for BPH/5 (n=12) and C57 (n=15) mothers allowed to go to term. Fetus numbers at different stages of pregnancy were analyzed by ultrasonography or by visualization at sacrifice. Fetal ultrasonography was performed in utero using an Acuson (Mountainview, Calif.) Sequoia c256 imager fitted with a 15 MHz linear array oscillator/receiver, yielding apparent in-plane resolution of ~0.1 mm. BPH/5 (n=15) or C57 (n=14) mice of 11 or more gestational days were grasped gently by the nape of the neck and cradled in the operator's left hand after receiving midazolam (0.3 mg SQ) prior to imaging. This procedure has been shown to produce no perturbation of adult murine heart rate or blood pressure, and eliminates the need for physical restraint of the animal during imaging. Hill et al., *Circ. Res.* 101:2863–9 (2000). Mice were imaged longitudinally starting at gestational day 11. Fetal demise was determined based on the following criteria: a) presence of homogeneous fluid contents of a fetal sac, b) decrease in the number of fetuses detected at successive time points during a given pregnancy, c) absence of fetal cardiac activity within a given sac after gestational day 12. Ultrasound findings were confirmed in a separate cohort that underwent necropsy during early (BPH/5 n=8, C57 n=7), middle (BPH/5 n=5, C57 n=6) or late (BPH/5 n=8, C57 n=9) gestation. A ventral midline incision was made, the uterine horn exposed, and fetuses were counted. Fetal resorptions, identified by necrotic/hemorrhagic appearance and smaller sizes compared to normal viable fetuses, were noted.

Analysis of Endothelium-dependent Vasodilation in vitro

Timed matings were carried out and vascular function studies performed in separate non-pregnant (BPH5, n=9; C57, n=8) or late gestational mice (BPH5, n=5; C57, n=5). Mice were sacrificed and mesenteric resistance arteries (~100 μm) were excised and cleaned of fat and connective tissue. Vessels were double-cannulated between two glass micropipettes, given intraluminal resting pressurization (20 mmHg), and placed in a 37° C. oxygenated Krebs bath. Vessels were pre-contracted with phenlyephrine ($10^{-7}$ M) followed by incremental doses of the endothelium-dependent vasorelaxant acetylcholine ($10^{-9}$–$10^{-6}$ M). Vessels were visualized via an inverted microscope connected to a closed-circuit video system and changes in luminal diameter measured using NIH Image®.

Data Analysis

Data are expressed as mean±SEM calculated for the gestational day or stage of pregnancy. Telemetry data are plotted as 24 hour averages every two days. Urinary protein levels are the average of two 24 hour samples for each mouse.

Ultrasonagraphic data were analyzed by assigning the number 1 to a pregnancy with at least one demise, the number 0 to pregnancies with no demises, and using Student's t-test. Litter sizes and pup weights were also analyzed by Student's t-test. Remaining data were analyzed by repeated-measures or one-way ANOVA followed by the Student's modified t-test with Bonferronni correction for multiple comparisons between means using the modified error mean square term from the ANOVA.

Results

BPH/5 Mice Developed Late Gestational Hypertension that Resolved After Delivery

A new radiotelemetric approach was recently developed for continuous hands-off recording of blood pressure longitudinally in pregnant unrestrained, untethered mice. Butz et al., *Physiol. Genomics* 5:89–97 (2001). It has been previously demonstrated that this is a reliable method for obtaining highly accurate blood pressure recordings during pregnancy without interfering with conception, gestation, delivery or postnatal care of neonates. Butz et al., *Physiol. Genomics* 5:89–97 (2001). Utilizing this technology, MAP was compared before, during and after pregnancy in BPH/5 and C57 mice (FIG. 1). Consistent with previous reports (Lester, J. W., SURVEY OF SELECTED PHYSIOLOGICAL PROPERTIES OF INBRED HYPERTENSIVE AND HYPOTENSIVE MICE," MA Thesis, Genetics Program, University of Kansas (1989); Butz et al., *Physiol. Genomics* 5:89–97 (2001)), BPH/5 had significantly elevated baseline MAP compared with controls prior to pregnancy (128±5 vs. 106±7 mmHg, p<0.01). MAP remained stable in both groups throughout the first 2 weeks of pregnancy. However, beginning in the last trimester (day 14), MAP began to rise even further in BPH/5 mice, continued to increase to peak levels just prior to delivery, and returned to pre-pregnancy levels by 2–3 days postpartum. In sharp contrast, MAP fell starting at the end of the second trimester in C57 mice for a short period, but returned to pre-pregnancy levels by several days prior to delivery where it remained throughout the postpartum period.

BPH/5 Mice Exhibited Renal Disease in the Last Trimester of Pregnancy

Figure 2:
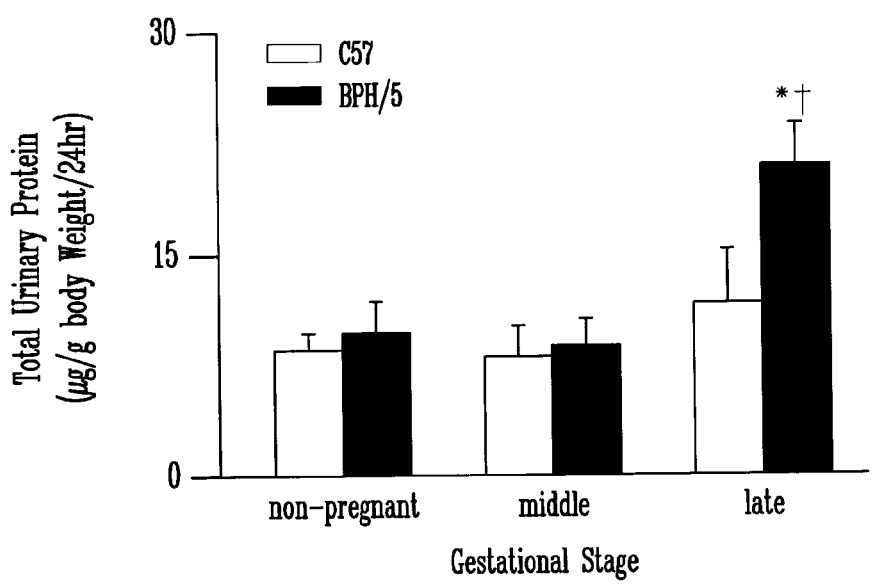
Figure 3:
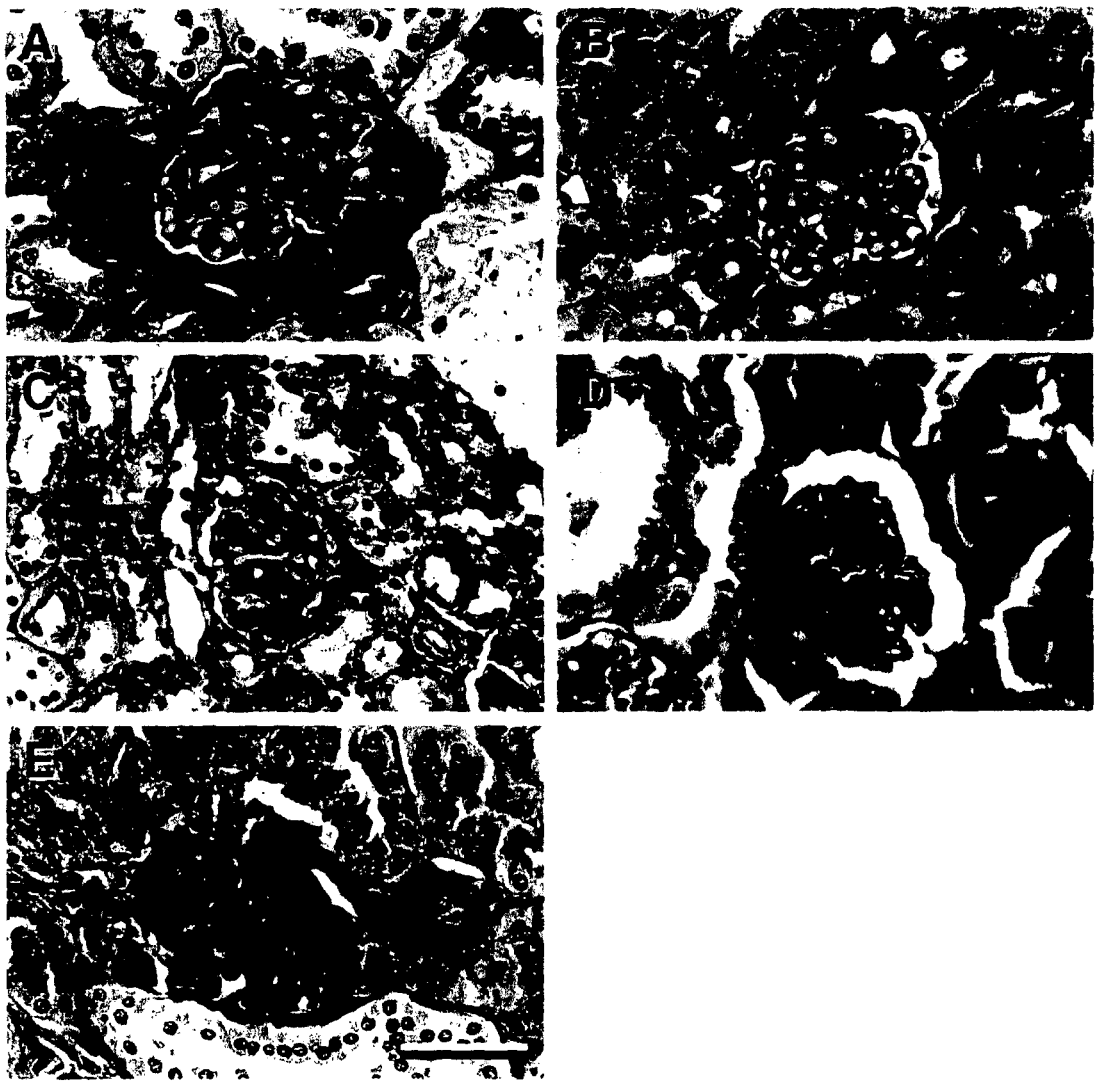

Because of the importance of proteinuria secondary to renal pathology in the diagnosis of preeclampsia (Roberts et al., *Lancet* 357:53–6 (2001)), urinary protein levels and renal histopathology were analyzed. Prior to pregnancy, C57 and BPH/5 mice had similar total urinary protein levels and these remained unchanged through mid-gestation (FIG. 2). However, by late stages of pregnancy (days 17–19), BPH/5 exhibited increased protein excretion compared to earlier timepoints, whereas C57 mice did not. Proteinuria was accompanied by marked renal histological changes by the start of the third trimester in BPH/5 mice (FIG. 3). By gestational day 14–15 in BPH/5, glomeruli showed early signs of focal and segmental sclerosis with collapse of glomerular capillaries (FIG. 3C). These changes were more often noted in the vascular pole of the glomeruli. Occasional glomeruli showed segmental adhesion of the collapsed glomerular tuft to Bowman's capsule. By day 19, these changes were more pronounced and ranged from focal and segmental glomerulosclerois (FIG. 3D) to global sclerosis (FIG. 3E). Glomeruli showed prominent focal and segmental sclerosis with collapse of glomerular capillaries and accumulation of PAS-positive hyaline material in the collapsed capillaries. In addition, the afferent/efferent arterioles of these glomeruli showed accumulation of PAS-positive hyaline material in the walls (FIGS. 3D and E). In contrast, kidneys from C57 mice showed normal glomeruli with open glomerular capillary loops, normal cellularity and delicate mesangium (FIG. 3A), and no changes were observed at any stage of pregnancy in these mice. Non-pregnant and early gestational BPH/5 mice showed similar normal renal histology (FIG. 3B). It should be noted that the extraglomerular interstitium of kidneys from late gestation BPH/5 mice did not show significant changes; in particular there is no evidence of sclerosis of the larger vessels.

Figure 4A:
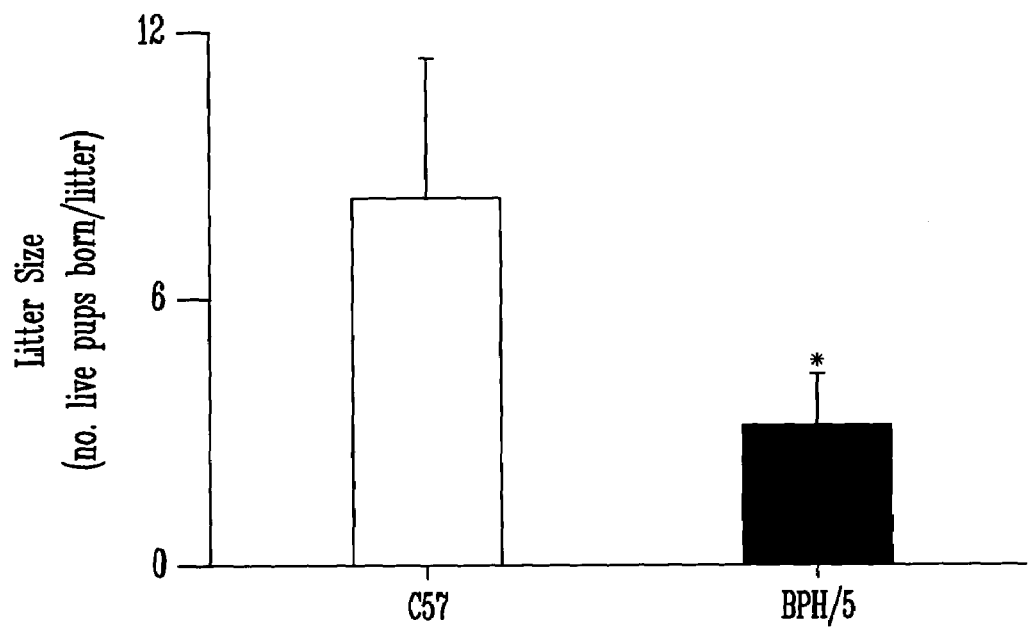
Figure 4B:
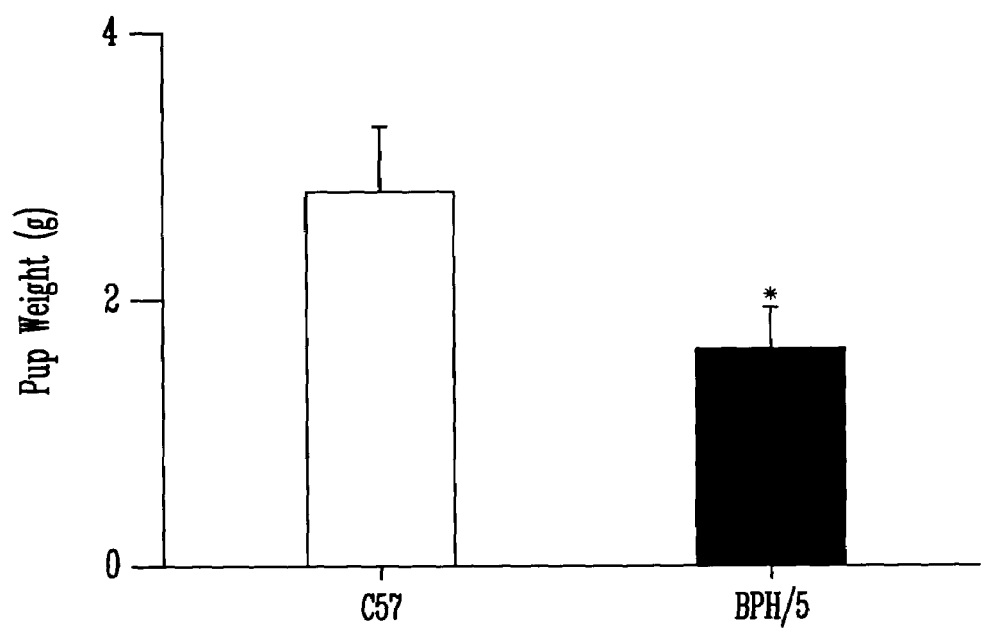
Figure 5A:
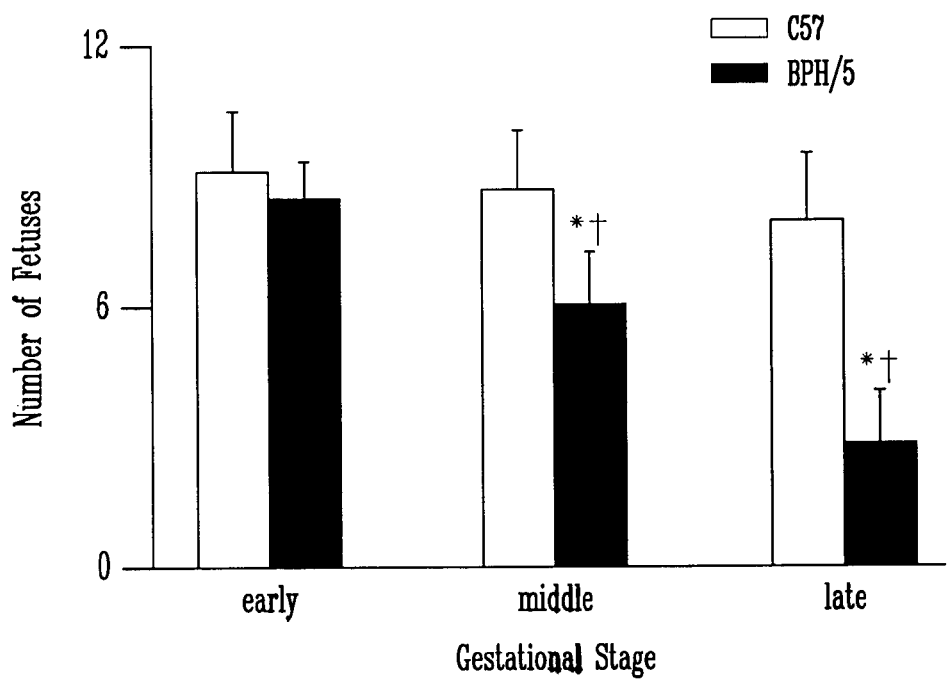
Figure 5B:
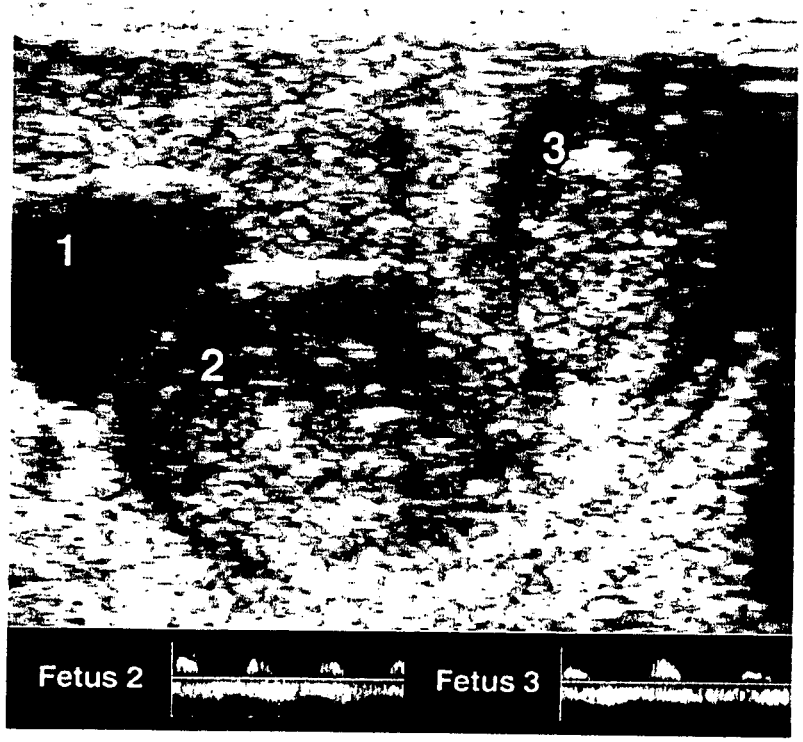

Intrauterine Fetal Demise, Small Live-born Litters, and Low Birth-weight Pups Were Observed in BPH/5 Pregnancies Preeclampsia is associated with perinatal morbidity and mortality and increased risk of poor fetal growth. National High Blood Pressure Education Program Working Group Report on High Blood Pressure in Pregnancy, *Am. J. Obstet. Gynecol.* 163:1691–1712 (1990). Thus, litter sizes, neonatal weights, and fetus numbers were examined at different stages of pregnancy. BPH/5 mothers delivered significantly smaller litters of live pups compared to C57 (FIG. 4A), and of those BPH/5 pups born, the average body weight was significantly less than that of C57 (FIG. 4B). To determine whether reduced litter sizes were due to failure to conceive, failure to implant or fetal demise, fetuses were examined in utero by ultrasound or visually at sacrifice. BPH/5 and C57 mice had similar numbers of fetuses early in gestation, but BPH/5 had progressively fewer viable fetuses at middle and late gestation (FIG. 5A). Evidence of fetal resorption was commonly observed during middle and late pregnancy in BPH/5 mice, whereas it was rare in C57 at any timepoint (data not shown). These findings were confirmed in ultrasound studies of a separate cohort in which BPH/5 and C57 fetuses were followed longitudinally. In a typical image of a BPH/5 mouse at day 12 of gestation (FIG. 5B), fetuses of varying status were observed. Fetus 2 was an apparently healthy and of normal size for this stage. Pulse-wave Doppler interrogation of umbilical blood flow (bottom panels) revealed a typical murine fetal heart rate (200 $min^{-1}$). In contrast, signs of fetal distress were observed in Fetus 3. In addition to being small for this stage, it was bradycardic (140 $min^{-1}$). The fetal sac on the left (labeled "1") contained homogeneous fluid, indicating completed fetal demise and autolysis. Interestingly, ultrasound images of the same BPH/5 mouse a week later revealed a single large empty sac without septa and no apparently viable fetuses (data not shown). Indeed, there were no pups born of this pregnancy. Overall, ultrasonographic evidence of fetal demise was detected in 13/15 pregnant BPH/5 mice studied starting gestational day 11, but in only 2/14 pregnant C57 mice ($p<0.0001$).

BPH/5 Exhibited Endothelial Dysfunction During Late Pregnancy

Figure 6:
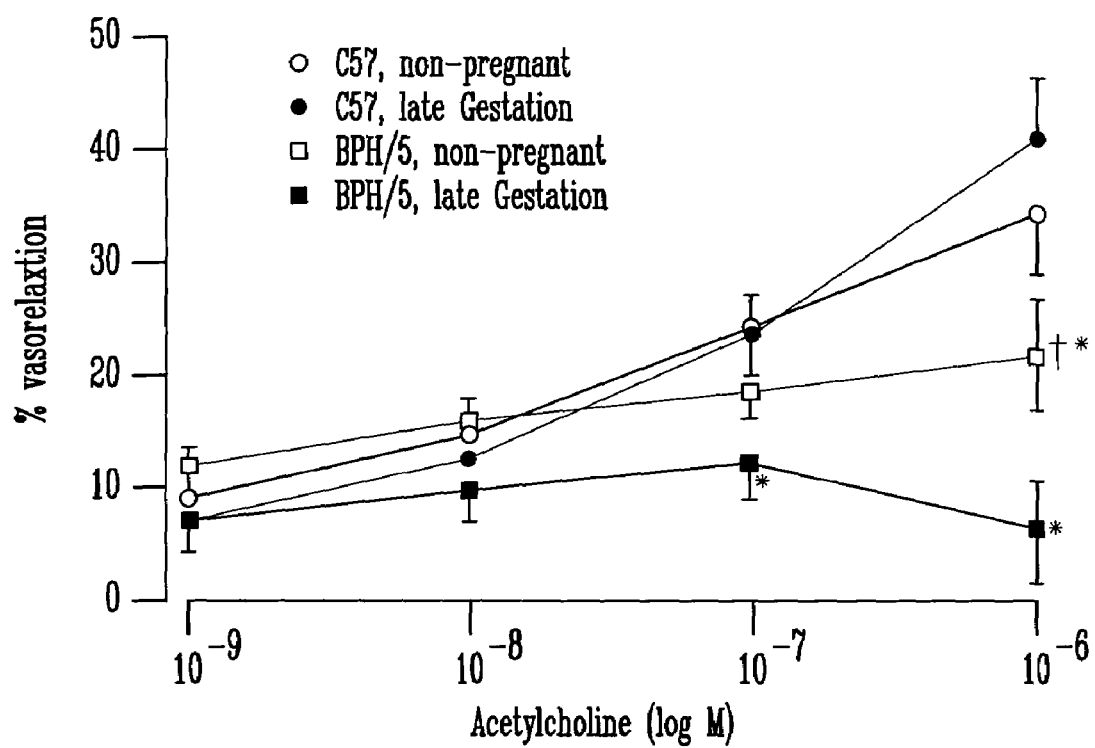

Since another hallmark of preeclampsia is the development of widespread maternal endothelial dysfunction (Roberts et al., *Lancet* 357:53–6 (2001)), endothelium-dependent vasorelaxation to acetylcholine in BPH/5 and C57 mice was examined. Endothelium-intact mesenteric resistance arteries from BPH/5 mice at 19 days gestation showed diminished relaxation compared to C57 vessels at the same timepoint (FIG. 6). Dose-response curves showed not only poor relaxation to acetylcholine, but also an early transition to acetylcholine-induced contraction, both suggestive of endothelium dysfunction. While vessel segments from non-pregnant BPH/5 showed a somewhat blunted response to the highest dose of acetylcholine compared to non-pregnant C57 mice, pregnancy induced a striking decrease in endothelium-dependent relaxation in BPH/5 while having little effect on C57 mice. Vessels obtained from early gestation mothers were indistinguishable from non-pregnant mice (data not shown). Relaxation to the endothelium-independent nitrovasodilator sodium nitroprusside was not different between groups, nor were there differences in the contractile response to acetylcholine in vessel segments denuded of endothelium by intraluminal infusion of air bubbles (data not shown).

Discussion

Preeclampsia is a serious hypertensive complication of pregnancy that increases maternal and perinatal morbidity and mortality. The etiology and pathogenesis of preeclampsia remain poorly understood, leading to the search for appropriate experimental models to study this disorder. This is the first report of a non-primate animal model that spontaneously exhibits relevant clinical features of human preeclampsia. Pregnant BPH/5 mice, an inbred substrain of the genetically hypertensive model BPH/2 (Schlager et al., *FASEB J.* 3:A1315 (1989); Lester, J. W., SURVEY OF SELECTED PHYSIOLOGICAL PROPERTIES OF INBRED HYPERTENSIVE AND HYPOTENSIVE MICE," MA Thesis, Genetics Program, University of Kansas (1989); Schlager, "Genetic hypertension in mice," in HANDBOOK OF HYPERTENSION, pp. 158–72, Ganten et al., eds., Elsevier, Amsterdam, Netherlands (1994)), develop hypertension, proteinuria, glomerular disease, and endothelial dysfunction. Intrauterine fetal demise and growth retardation are also observed.

Many attempts have been made to generate animal models of preeclampsia, including uteroplacental ischemia (Losonczy et al., *Hypertension in Preg.* 12:475–85 (1993); Clark et al., *Am. J. Physiol.* 242:H297–H301 (1982)), chronic nitric oxide synthase inhibition (Yallampalli et al., *Am. J. Obstet. Gynecol.* 169:1316–20 (1993)), adriamycin nephropathy (O'Donnell et al., *J. Lab. Clin. Med.* 106:62–7 (1985)), and transgenic expression of human renin-angiotensin system genes (Takimoto et al., *Science* 274:995–8 (1996)). Each has been important for understanding certain aspects of the disease, although none recapitulate the full syndrome. Podjarny et al., *Sem. Perinatol.* 23:2–12 (1999). In most of these models, hypertension does not resolve upon delivery, and pathophysiological changes are observed both in pregnant and non-pregnant animals. Podjarny et al., *Sem. Perinatol.* 23:2–12 (1999). BPH/5 mice develop a syndrome only when pregnant that is strikingly reminiscent of the clinical disorder. The onset of hypertension and renal disease during the last trimester (third week) of pregnancy in BPH/5 corroborates the time-course of the clinical disorder. Furthermore, the return of elevated blood pressure to pre-pregnancy levels immediately following delivery in BPH/5 mice is also consistent with the definitive response of hypertension to delivery in humans. Taken together with knowledge that mice have the same unique hemochorial type of placentation as humans (Cross, *Sem. Cell. Dev. Biol.* 11:105–13 (2000), an important consideration since preeclampsia is thought to involve abnormal placentation, the BPH/5 strain is a promising new model to study this complex disease.

The long-term recording potential of radiotelemetry (Butz et al., *Physiol. Genomics* 5:89–97 (2001)) allowed the inventors to implant transmitters before mice were bred, provide adequate recovery time following surgery, and then record blood pressure continuously throughout pregnancy without interruptions such as restraint, handling or anesthesia/surgery. In the prepregnancy state, BPH/5 had baseline blood pressure levels that were intermediate between its hypertensive parent strain BPH/2 and normotensive controls. This corroborated earlier analyses of this model subsequent to its generation as an inbred subline of BPH/2. Schlager et al., *FASEB J.* 3:A1315 (1989); Lester, J. W., SURVEY OF SELECTED PHYSIOLOGICAL PROPERTIES OF INBRED HYPERTENSIVE AND HYPOTENSIVE MICE," MA Thesis, Genetics Program, University of Kansas (1989); Butz et al., *Physiol. Genomics* 5:89–97 (2001). Since preeclampsia manifests as new onset or worsening hypertension, and patients with borderline hypertension are known to be at increased risk to develop the disease (Reiter et al., *Am. J. Kid. Dis.* 24:883–7 (1994), the inventors were interested in whether this inbred borderline hypertensive strain would develop hypertension during pregnancy. Indeed, the increase in blood pressure at the start of the last trimester and subsequent rise to peak levels until delivery observed in BPH/5 is one of the heralding signs of preeclampsia. Roberts et al., *Lancet* 357:53–6 (2001). Given that pregnancy is actually antihypertensive during middle to late gestation both in normotensive and hypertensive women and animal models (Takeda, *Jap. Circ. J.* 28:49–54 (1964); Baylis, "Glomerular filtration and volume regulation in gravid animal models," in BAILLIERES CLINICAL OBSTETRICS AND GYNECOLOGY, VOL. 8, pp. 235–64, Lindheimer et al., eds., London, Ballieres Tindall (1994); Cunningham et al., "Hypertensive disorders of pregnancy," in WILLIAMS OBSTETRICS, pp. 693–744, Appleton & Lange, Stamford, Conn. (1997)), the rise in blood pressure is even more striking. Interestingly, a similar transient decrease in blood pressure early in the third trimester in C57 mice was observed, as reported in women. Cunningham et al., "Hypertensive disorders of pregnancy," in WILLIAMS OBSTETRICS, pp. 693–744, Appleton & Lange, Stamford, Conn. (1997).

A clinical diagnosis of preeclampsia includes not only an increase in blood pressure, but also proteinuria. Without proteinuria, a diagnosis of gestational hypertension is made. Roberts et al., *Lancet* 357:53–6 (2001). Although the significance of this classification with regard to pathogenesis is not clearly understood, it is an important consideration in establishing a model of preeclampsia. In the prepregnancy state and through mid-gestation, urinary protein levels were normal in BPH/5. However, proteinuria was detected during late gestation in these mice, concomitant with the rise in blood pressure, and consistent with clinical observations of proteinuria during the last trimester of pregnancy. In patients, this abnormality resolves upon delivery (Cunningham et al., "Hypertensive disorders of pregnancy," in WILLIAMS OBSTETRICS, pp. 693–744, Appleton & Lange, Stamford, Conn. (1997)), however this is a difficult parameter to measure in an early postpartum mouse since animals are removed from metabolic cages for delivery and care of pups. Early signs of renal histological changes in BPH/5 mice were first detected at the start of the last trimester (day 14–15), and became more pronounced during the last few days of pregnancy. Abnormalities ranged from focal and segmental glomerulosclerois to global sclerosis, reminiscent of pathological changes seen in kidneys of preeclamptic patients.

The inventors' studies indicate that BPH/5 mothers deliver significantly smaller litters of low birth-weight pups. This appears to be the result of intrauterine fetal demise and/or compromise rather than a failure of conception or implantation since BPH/5 have a normal number of fetuses in early gestation. Interestingly, demise began to occur prior to the onset of hypertension and renal disease. This supports a prominent theory suggesting that the primary defect in preeclampsia originates at the fetoplacental interface. Taylor et al., *Sem. Reprod. Endocrinol.* 16:17–31 (1998). Abnormal placental vasculature causes inadequate maternal-fetal circulation, leading to intrauterine fetal compromise. This is thought to result in the release of fetoplacental factors that damage the maternal vascular endothelium, which leads to the various systemic manifestations of preeclampsia. Chambers et al., *JAMA* 285:1607–12 (2001). Interestingly, the in vitro vessel data show that BPH/5 also exhibits a striking pregnancy-related impairment in endothelial function. It is believed that this model, coupled with noninvasive longitudinal analysis of fetal status using ultrasonography, may provide the opportunity to experimentally test this theory.

The major contribution of this study is the characterization of an animal model that bears a close pathophysiological resemblance to the clinical disorder preeclampsia. Given that preeclampsia likely has an important genetic component (Morgan et al., *Sem. Perinatol.* 23:14–23 (1999)), this inbred genetic strain provides a particularly exciting opportunity for studying its molecular genetic pathophysiology. Furthermore, the model should prove useful for preclinical testing of therapeutic approaches to this disorder.

EXAMPLE 2

In this study we hypothesized that BPH/5 mice would exhibit abnormalities in early placental development and growth compared to C57BL/6 controls. We further postulated that these changes would be associated with dysregulation of the normal placental vascular gene profile. The BPH/5 mouse model offered us the unique ability to examine the placental architecture and gene expression profiles at multiple time points throughout gestation. Moreover, the mouse placenta is hemochorial and its layers appear to be functionally analogous to those in the human placenta, (Rossant et al., *Nature Reviews Genetics* 2:538–548 (2001)), allowing us to make comparisons with human placental abnormalities detected in preeclampsia. We have used morphometric, immunohistochemistry, molecular analyses and Doppler flow studies to address this hypothesis in detail.

Methods

Animals and Husbandry

Experiments were performed in female (19- to 24-g) C57BL/6 (C57) or BPH/5 mice, an inbred subline derived from spontaneously hypertensive strain, BPH/2. Davisson et al. *Hypertension* 39 (part 2):337–42 (2002). Timed matings were performed by pairing strain-matched males and females overnight as described previously. Davisson et al. *Hypertension* 39 (part 2):337–42 (2002). The morning of detection of a vaginal plug was designated embryonic day 0.5 (E0.5). All cohorts of animals were comprised of both primiparous and multiparous animals. Care of the mice met the standards set forth by the Guide for the Care and Use of Laboratory Animals of the National Institutes of Health. The University Animal Care and Use Committee at the University of Iowa approved all procedures.

Immunohistochemistry and Electron Microscopy

BPH/5 and C57 mice were sacrificed by $CO_2$ asphyxiation at gestational time points from E9.5–19.5. At the earlier time points (up to E12.5), the entire uterine horn was removed, cut between implantation sites and immersed en bloc in 10% neutral buffered formalin for fixation. At later gestational ages only the placenta was dissected, fixed and then embedded in paraffin. Tissues were sectioned (4u) and stained with hematoxylin and eosin for general morphology. The following antibodies were used for immunohistochemistry: Biotinylated Griffonia Simplicifolia Isolectin B4 (dilution 1:125, Vector Laboratories, Burlingame, Calif.) to label the basement membrane of fetal endothelial cells in the labyrinthine zone and p57$^{KiP2}$Ab-3 (dilution 1:100, Lab Vision Corporation, Fremont, Calif.) to stain the spongiotrophoblasts cells invading into the maternal deciduas. Georgiades et al., *PNAS* 98:4522–4527 (2001). Periodic Acid Schiff (PAS) was used to stain the granules in the uNK cells residing in the deciuda (Croy et al., *J. Soc. Gynecol. Investig.* 7:12–20 (2000)), the glycogen positive cells and fibrin deposits in the spongiotrophoblast and labyrinthine layer.

The immunohistochemical staining was performed on a Dako Autostainer (Dako, Carpinteria, Calif.) as per the manufacturer's instructions. Briefly, after antigen retrieval and blocking, the slides were incubated with anti-isolectin B4 for 120 minutes, rinsed in TBST, followed by incubation with RTU Vectastain ABC peroxidase conjugated streptavidin reagent (Vector Laboratories) for 20 minutes. Similarly, after antigen retrieval and blocking, slides were incubated with p57$^{Kip2}$ antibody for 30 minutes, rinsed in TBST, followed by incubation with M.O.M. biotinylated anti-mouse IgG reagent for 20 minutes and then Streptavidin Vectastain Elite ABC Peroxidase conjugated reagent. For both antibodies the slides were stained with DAB+ {Brown} Substrate (Dako) for 5 minutes and counterstained with Mayer's Hematoxylin. Periodic Acid Schiff (PAS) staining was performed by standard protocol. Davisson et al., Hypertension 39 (part 2):337–42 2002.

For transmission electron microscopy (TEM) semithin sections (1 μm) were obtained from placentae, fixed in Kamovsky's fixative for 24 hours followed by post fixation in 1% OsO4 with 1.5% Potassium Ferrocyanide. The sections representing the labyrinthine layer were analyzed in detail. Georgiades et al., PNAS 98: 4522–4527 (2001).

Morphometric Analysis

Whole placental weights were measured by dissecting out the placenta from the uterine horn prior to tissue fixation at E9.5, E14.5 and E18.5. Morphometric analysis of placentas from BPH/5 and C57 mice at corresponding gestational time area of the ST layer the fetal labyrinth was first measured by tracing the area stained with isolectin B4 (L). Then the area of the entire placenta between the chorioallantois and the GC layer was measured (ST+L). These measurements allowed us to derive the area of the spongiotrophoblast layer alone (ST), and then express it as a ratio of the entire placental area (ST/ST+L). All measurements were made in a blinded-fashion and independently by two authors (AD, DH) and the mean values were used for statistical analysis.

Quantitative Real Time PCR

BPH/5 and C57 mice were sacrificed and placentas collected for RNA isolation: i) pooled extraembryonic tissues were isolated from E9.5 conceptuses including the ectoplacental cone, amnion, chorion, trophoblast, and decidua, but excluding the embryo proper; and ii) whole placentas from E14.5 and E19.5 including decidua, but free of myometrium. Placentas from each litter (n=3) were pooled, homogenized in TRIZOL® reagent (Molecular Research Center, Cincinnati, Ohio) and purified (Rneasy spin column, Qiagen, Chatsworth, Calif.). DNAse treated RNA (DNA-free, Ambion, Your Town, USA) was quantified, reverse transcribed using T7-oligo (dT) primers and amplified using SYBR Green (PE Biosystems, Your Town, USA) with primers shown in Table 1.

TABLE 1

Primers used for real time PCR to compare placental gene expression between BPH/5 mice and C57 controls.

| Target gene | Forward Primer | Reverse Primer |
| --- | --- | --- |
| Placental Lactogen (PL) 1 | 5'-GAAATGCAGCTGACTTTGAATCTT-3' SEQ ID NO:1 | 5'-GGCTTGACACCAGCAGCA-3' SEQ ID NO:2 |
| Placental Lactogen (PL) 2 | 5'-TGGACCTATGGCCTGATGTTAA-3' SEQ ID NO:3 | 5'-TTGCTCGCTGTTTTCTGGAGT-3' SEQ ID NO:4 |
| Insulin-like Growth Factor 2 | 5'-GGGAGCTTGTTGACACGCTT-3' SEQ ID NO:5 | 5'-CGGCTTGAAGGCCTGCT-3' SEQ ID NO:6 |
| Proliferin (PRF) | 5'-GGCTCACACACTATTCAGCTCTTC-3' SEQ ID NO:7 | 5'-CGTCCAGAGGGCTTTCCC-3' SEQ ID NO:8 |
| Proliferin-related protein (Prp) | 5'-TGAAGCATCTCCCCGGAA-3' SEQ ID NO:9 | 5'-GTTGGATCAAAGAAGGGAGCAT-3' SEQ ID NO:10 |
| VEGF | 5'-CATCTTCAAGCCGTCCTGTGT-3' SEQ ID NO:11 | 5'-CAGGGCTTCATCGTTACAGCA-3' SEQ ID NO:12 |
| sFlt-1 | 5'-CCTCATTGTCCTTGGCTGGA-3' SEQ ID NO:13 | 5'-TTATAATGAAGGCTTGCTGCACTT-3' SEQ ID NO:14 |
| Adrenomedullin | 5'-CATTGAACAGTCGGGCGAGTAT-3' SEQ ID NO:15 | 5'-CCCCGGTGCGAAGTTCT-3' SEQ ID NO:16 | points was performed with an NIH image analysis system (Scion Image). Special care was taken to place all placentas in a similar orientation prior to embedding, and measurements were performed on sections representing the central most portion of each placenta. All sections used for morphological analysis were stained with the antibody to isolectin B4 in order to identify the fetal vessels in the labyrinthine zone (L). The spongiotrophoblast layer (ST) was seen between the labyrinth and the outer giant cell (GC) layer. The GC layer defined the outer border of the placenta and the chorioallantois (CA) formed the base of the placenta. The width of the placenta (P) was determined by first drawing a line along the base of the labyrinth, identifying the midpoint of this line and drawing a perpendicular up to the GC layer and extending it to the outer edges of the decidua (De). The width of the placenta (P) was then expressed relative to the width of the placenta and decidua (P/P+De) at selected gestational time points. In order to determine the Primers were selected using the Primer express software (Applied Biosystems, Your Town, USA) and forty cycles of PCR were performed (50, 2 min; 95, 10 min; 40× [95, 0:15 min; 61, 1 min]) followed by a dissociation protocol. Each sample was run in triplicate and gene expression was reported according to the standard curve method described previously by Applied Biosystems (User Bulletin #2). Message levels were normalized to 18S and then directly compared between C57 and BPH/5 placentas. Sequence-specific amplification was confirmed by gel analysis of PCR products and single peak formation during the dissociation protocol following amplification.

Ultrasound Assessment of Uterine Arterial Blood Flow

Doppler ultrasound was performed with an Acuson Sequoia c256 imager fitted with a 15-MHz linear array oscillator/receiver, yielding an apparent in-plane resolution of ≈0.1 mm. BPH/5 (n=6) or C57 (n=7) mice at E16.5 were administered subcutaneous midazolam (0.3 mg), then held gently by the nape of the neck and cradled in the operator's hand. This procedure produces no perturbation of adult murine heart rate or blood pressure, no known teratogenic effects, and eliminates the need for stressful physical restraint of the animal during the procedure. Hill et al., Circulation 101(24):2863–9 (2000). A large uterine artery was identified by the meridian color-flow along the external uterine wall. Echo Doppler resolution gates were placed around the uterine arteries and 1-second Doppler waveforms were collected for analysis. Pulsatility index (PI) was derived from the waveforms (PI=Systolic Flow/Diastolic Flow) as with the standard clinical approach, and converted to Resistive Index (RI=1−[1/PI]).

Statistical Analysis

Data are expressed as mean±SEM. Statistical significance for morphometric studies and Doppler analysis was determined by using the student's T test and the p value was significant at 0.05.

Results

Immunohistochemistry and Morphometric Analysis

BPH/5 Mice Have Markedly Reduced Placental Weights

We have previously described smaller litter sizes and reduced fetal weights in BPH/5 mice compared to C57 controls. Davisson et al., Hypertension 2002;39 (part 2):337–42. In this study we sacrificed both BPH/5 and C57 mice at different gestational ages and weighed whole placentas prior to using them for further analysis (Table 2).

TABLE 2

Placental weights in C57 controls and BPH/5 mice at different gestational time-points.

| Gestation Day | C57 | BPH/5 |
| --- | --- | --- |
| E9.5 | 14.65 ± 0.22 (17) | 5.83 ± 0.14 (12)* |
| E14.5 | 117.47 ± 1.69 (20) | 65.83 ± 6.42 (25)** |
| E19.5 | 109.23 ± 1.54 (13) | 115.55 ± 4.31 (22) |

Values are expressed in grams and mean ± SEM. Total numbers of placentas measured are in parenthesis.
*p < 0.05,
**p < 0.01

Placental weights were reduced by 40–50% at E9.5 ($p<0.05$) and E14.5 ($p<0.01$) in the BPH/5 mice as compared to C57 mice. Using combined immunohistochemical and morphometric analysis the depth of the placental disc (P) and decidua (De) were also measured. In the BPH/5 mice the proportional width of the placentas was reduced in size as early as E10.5 and up to E18.5. These results indicate that placental pathology reflected by reduced weights and restricted expansion towards the decidua in the BPH/5 strain was present at or before E12.5, prior to the detection of hypertension and proteinuria.

Significantly Smaller Spongiotrophoblast Layers in BPH/5 Mice Throughout Gestation To determine the etiology for the dramatic reduction in placental weights in the BPH/5 mice we focused our initial studies on detailed examination of all three zones of the placenta (labyrinth (L), spongiotrophoblast (ST) and giant cell (GC) layer) along with the decidua (De). All placental cell lineages were present in both groups of mice. Using standard histology, immunohistochemistry and electron microscopy we found morphological abnormalities in all zones of the placenta and decidua in the BPH/5 strain.

However, we found the reduction in the placental width to be predominantly due to a decrease in the area of the ST layer in the BPH/5 mice. Morphometric analysis revealed a striking reduction in the fractional area represented by the ST layer (ST/ST+L) within the BPH/5 placentae at all gestational ages compared to C57 controls. Histological examination of the ST layer revealed the presence of both PAS-positive vacuolated cells (glycogen cells) and non-vacuolated eosinophilic cells (spongiotrophoblasts), indicating that loss of a specific cell type did not contribute to the observed reduction in the size of this layer.

In the ST layer of the mouse placenta a subset of the vacuolated spongiotrophoblasts exhibit interstitial invasion of the decidua and stain positively with the antibody to $p57^{Kip2}$ (cyclin dependent kinase inhibitor). Georgiades et al., PNAS 98: 4522–4527 (2001). Since $p57^{Kip2}$ plays a role in cell proliferation in the labyrinthine and ST layers, (Takahashi et al., Mol Hum Reprod 6: 1019–1025 (2000)), we examined the pattern of $p57^{Kip2}$ staining in the BPH/5 and C57 placentas. The earliest evidence of $p57^{Kip2}$ nuclear staining in the ST layer of C57 placentas was seen at E14.5 and these cells demonstrated diffuse invasion beyond the GC layer into the decidua. In contrast, at the same gestational time point BPH/5 placentas had only occasional $p57^{Kip2}$-positive cells in the ST layer, the GC layer appeared more continuous, with few $p57^{Kip2}$-positive cells in the decidua. This difference in $p57^{Kip2}$ staining persisted up to E18.5 (data not shown).

Decreased Branching and Expansion of the Fetal Vessels in the Labyrinth of BPH/5 Mice The labyrinthine zone consists of cells of trophoblast and mesodermal origin that together undergo branching morphogenesis resulting in a large surface area for nutrient and gas exchange. As early as E10.5 the labyrinth comprises of vascular beds with nucleated fetal erythrocytes intermingled with maternal blood spaces containing mature erythrocytes. We used anti-isolectin B4 to identify the fetal endothelial cell basement membranes and electron microscopy to examine the labyrinth. At E12.5 in C57 placentas the labyrinth had uniformly elongated fetal vessels with elaborate branching morphogenesis, which is responsible for increasing the placental area to match the increase in maternal blood flow. Decreased morphogenesis of fetal vessels and impaired depth of expansion of the labyrinthine zone towards the ST layer was evident in BPH/5 placentas. As a result the junction of the expanding labyrinth and the ST layer was very uneven in BPH/5 placentas but smooth in C57 placentas (picture not shown). With increasing gestational age the fetal vessels in the C57 placentas were seen to uniformly advance towards the trophoblast such that maternal and fetal blood spaces were only separated by a few trophoblast cells. In contrast, in the labyrinth of BPH/5 placentas PAS-positive broad trabecular columns were seen between fetal vessels in early gestation and smaller clusters of trophoblast cells persisted up to E19.5.

Ultra structural examination of the labyrinth allows visualization of the feto-maternal interface comprising of three trophoblast layers and fetal capillary endothelium. Georgiades et al., PNAS 98: 4522–4527 (2001). Fewer fetal and maternal blood spaces per field were seen in BPH/5 at E14.5 as compared to the C57 placentas. All three trophoblast layers were easily identified in C57 placentas and were uniform in appearance. The trophoblast layer closest to the fetal basement membrane (t1) and the middle trophoblast layer (t2) were of uniform thickness with several focal junctional areas between them. The outermost trophoblast layer (t3) was more loosely attached and in contact with the maternal blood space. Examination of BPH/5 placentas revealed less distinct and irregular trophoblast layers in several fields (FIG. 2H). The middle trophoblast layer (t2) appeared attenuated compared to the C57 placentas. Both t1 and t2 showed irregular short projections arising from the cell surfaces giving the layers a 'porous' appearance as shown by the arrows. Similarly there were several elongated processes arising from the outer most trophoblast layer (t3). These processes may represent a compensatory adaptation to increase the surface area for exchange. The fetal endothelium and its basement membrane was not thickened and appeared continuous in both BPH/5 and C57 placentas.

Vascular Changes Associated with Pregnancy Were Less Evident in the Decidua of BPH/5 Mice During pregnancy modification of spiral arteries occurs as they traverse the decidua. This is characterized by a loss of elastin and smooth muscle cells in order to facilitate an increase in maternal blood flow towards the developing placenta. Examination in the BPH/5 mice at E12.5 showed that several maternal blood vessels seen in the outer half of the decidua retained the smooth muscle layers giving them a 'cuffed' appearance (data not shown). Dilated maternal blood spaces were more evident in the decidua proximal to the GC layer in the BPH/5 mice. Areas of linear necrosis were also seen within the decidual layer of BPH/5 mice accompanied by extravasations and PAS-positive fibrin deposits. Similar fibrin deposits were also noted in the fetal labyrinthine blood spaces in BPH5 placentas as early as E12.5. These fibrin deposits were rarely seen in C57 placentas.

Granulated uterine natural killer (uNK) lymphocytes may facilitate vasodilatation of spiral arteries in the decidua. Croy et al., J. Soc. Gynecol. Investig. 7:12–20 (2000). They are abundant in the mouse decidua with peak numbers around E12–14. We examined their distribution using PAS to identify the granulated uNK cells in the decidua. PAS-positive granulated cells were widespread throughout the decidua in C57 and BPH/5 mice with a similar pattern between E10.5–14.5. By E15.5–17.5, the BPH/5 placentas showed fewer PAS-positive cells compared to the controls. Overall, the maternal decidua was narrower in width and more vacuolated in the C57 controls but had a broad but compact appearance in the BPH/5 mice at E12.5. These findings may be secondary to the reduced placental expansion towards this region noted in the BPH/5 strain.

Molecular Analysis for Placental Gene Expression

Imbalance Between Genes Responsible for Activation and Inhibition of Angiogenesis in the Placentas of BPH/5 Mice To test the hypothesis that the observed placental abnormalities in the BPH/5 mice may be associated with dysregualtion of the placental gene profile we compared time-matched samples of BPH/5 and C57 placentas using the Affymetrix Mu_U74Av5 gene chips. Regulators of angiogenesis such as VEGF, PlGF and s-FLT 1 may be critical for early placental development and even controlling events such as pseudovasculogenesis, mimicking of the endothelial cell phenotype by human trophoblasts. Zhou et al., Am J Pathol 160:1405–1423 (2002). Hence we selected genes responsible for activation and inhibition of angiogenesis from our microarray database and performed real time RT-PCR to confirm the expression of the gene targets summarized in Table 3.

TABLE 3

Real time PCR results expressed as a fold difference between C57 and BPH/5 placentas.

| Gene | E9.5 | E14.5 | E19.5 |
|---|---|---|---|
| Placental Lactogen (P1) -1 | −112.4 ± 79 | −21.3 ± 1.1 | −27.9 ± 20.2 |
| Placental lactogen (PL)-2 | −239.4 ± 222.9 | −11.5 ± 7.8 | −0.003 ± 0.9 |
| Insulin-like growth factor -2 | −33.1 ± 16.2 | −112.1 ± 109.96 | 0.17 ± 1.5 |
| Proliferin (PLF) | −67.7 ± 9.7 | −9.8 ± 6.7 | −2.3 ± 0.7 |
| Proliferin related protein (Prp) | −27.3 ± 14.9 | −30.2 ± 25.1 | 0.39 ± 1.2 |
| VEGF | −2.1 ± 0.5 | −7.2 ± 5.1 | −3.3 ± 4.2 |
| sFlt-1 | 2.6 ± 1.2 | −4.5 ± 1.1 | 2.4 ± 0.8 |
| Adrenomedullin | −6.3 ± 3.8 | −16.9 ± 18.3 | 0.5 ± 1.6 |

The values are expressed as mean ± SEM.

Expression of trophoblast gene products important for mouse placental development, namely placental lactogen (PL) 1, PL-2 and insulin-like growth factor (IGF) 2 were markedly reduced at E9.5 and 14.5 in BPH/5 placentas (Table 3). Proliferin (PLF), a member of the prolactin/growth hormone gene family, which plays a role in early placental angiogenesis, was found to be predominantly decreased (>60 fold) at E9.5. Proliferin related protein (Prp), an antagonist PLF was also reduced at E9.5 and 14.5 but to a lesser extent than PLF. In most tissues the net angiogenic effect is controlled by the balance between angiogenic inducers and inhibitors. In order to assess the combined effects of these two factors in the early developing placenta, we analyzed the ratio of the mean PLF expression to the mean Prp expression at E9.5, and determined the net angiogenic activity (PLF/Prp) to be markedly reduced in BPH/5 (4.9) compared to C57 placentas (19.5). Another pair of known angiogenesis regulators is VEGF and s-Flt1. VEGF expression was reduced throughout gestation in BPH/5 placentas however, s-FLT1 was unchanged at E9.5 and E19.5 and expressed at lower levels only at E14.5. Alterations in the ratio of VEGF and s-Flt1 expression affect the number of implantation sites and fibrin deposition in mouse placentas. He et al., Mol Endo 13:537–545 (1999). In our study we were unable to determine the ratio of VEGF to s-FLt-1 due to differences in primer characteristics. Finally, adrenomedullin, a peptide vasodilator, was markedly decreased in BPH/5 placentas at E9.5 and 14. Taken together, these findings suggest an early and persistent dysregulation in key vascular and developmental transcripts. Again, these changes were seen earlier than the detection of hypertension and proteinuria.

Uterine Artery Doppler Flow Analysis

Decreased Blood Flow in Uterine Arteries of BPH/5 Mice

In the mouse the blood supply to the placenta originates from the radial artery, a branch of the uterine artery. Further branches of the radial artery pass laterally in the myometrium or traverse into the myometrium and enter the metrial triangle of each implantation site. In normal pregnancies a change in the diameter of these vessels occurs around midgestation to facilitate an increase in blood flow to the developing fetus. Adamson et al., Dev Biol 250:358–373 (2002). To test the hypothesis that the observed placental abnormalities and poor pregnancy outcomes in BPH/5 mice are linked to compromised maternal-placental circulation, we utilized Doppler ultrasound to noninvasively examine blood flow in uterine arteries. Doppler ultrasound assessment of uterine artery blood flow at E16.5 showed peak blood flow during systole and reduced flow during diastole in C57 pregnant mice compared to near-cessation of diastolic flow in uterine arteries of BPH/5 mice. The PI is commonly used as an indicator of vascular resistance downstream from the artery interrogated (Tekay, 2000). We calculated the RI for our data because diastolic flow was often equal to zero in BPH/5 mice, resulting in an undefined PI. The mean calculated RI in BPH/5 mice was significantly increased ($p<0.05$) compared to C57 controls. These findings suggest that placental vascular insufficiency in BPH/5 mice is due to increased down stream resistance, which may contribute to the fetal growth restriction and demise observed in this mouse model of preeclampsia.

Discussion

In this study we tested the hypothesis that impaired placental development is an early hallmark in the BPH/5 mouse model of preeclampsia. We examined placental histology and morphometrics, expression of placental vascular and developmentally related genes and uterine artery blood flow patterns in these mice. BPH/5 mice have late-gestational hypertension, proteinuria, endothelial dysfunction and small litter sizes with reduced fetal weights compared to C57 controls. Davisson et al., Hypertension 39 (part 2):337–42 (2002). In this study, detailed histological evaluation of the placentas revealed significantly narrow ST layers contributing to the decreased width and weight of the placenta in BPH/5 mice. In addition, reduced vascular density was evident in the placental labyrinth as characterized by decreased branching and expansion of the fetal vessels towards the trophoblast. Second, genes critical for the synthesis of hormones that play a role in early placental angiogenesis and development were downregulated by mid gestation. Third, we found reduced uterine blood flow and impaired remodeling in some maternal uterine vessels. Collectively, these findings in BPH/5 mice suggest significantly compromised placental development as early as E9.5–12.5, namely prior to the onset of signs of preeclampsia such as hypertension and proteinuria.

The mouse placenta serves as an excellent model to study human placental pathology. Rossant et al., Nature Reviews Genetics 2:538–548 (2001). The trophoblast giant cells are analogous in function to extravillous cytotrophoblasts of the human placenta. They lie at the periphery of the feto-placental unit and mediate the process of implantation and invasion. The intermediate ST layer contains cells probably analogous to the anchoring trophoblast cell columns in human placentas. The labyrinthine layer is analogous to the chorionic villi in the human placenta with maternal blood perfusing trophoblast-lined spaces, which are in close proximity to fetal blood spaces, making the mouse placenta hemochorial as seen in primates. In addition, maternal blood circulation patterns through the human and mouse placentas show many similarities. Adamson et al., Dev Biol 250: 358–373 (2002). The strength of our study was in the ability to examine differences in placental morphology and gene expression profiles at several early time points in gestation. Our data was based on examination of the entire placenta and not restricted to limited placental bed biopsies.

The initiating event in preeclampsia has been postulated to be reduced uteroplacental perfusion as a result of abnormal cytotrophoblast invasion of spiral arterioles. Zhou et al., J Clin Invest 99:2152–2164 (1997). In our study we observed a significant increase in uterine artery resistive indices in the BPH/5 strain at E16.5 compared to C57 controls. This time period corresponds to the time of detection of hypertension but was earlier than detection of proteinuria in the BPH/5 strain. Davisson et al. Hypertension 39 (part 2):337–42(2002). It is possible that uterine blood flow was reduced earlier in gestation however, we were technically limited in our ability to accurately perform uterine artery Dopplers earlier than E16.5. Iatrogenic reduction in uterine blood flow in a number of animal models has also been shown to induce a hypertensive state that closely resembles preeclampsia. Conrad et al. Fetal Med Rev 2 pp. 67–88 (1990); Abitbol et al., Clin Exp Hyper Hyper Preg B1 pp. 93–103 (1982). Emerging data on uterine artery Doppler studies in pregnant women also give credence to our findings. Increased uterine artery resistance and decreased blood flow documented by doppler ultrasound is predictive of high risk human pregnancies associated with intrauterine growth restriction (IUGR). Mires et al., Am J Obstet Gynecol 179:1317–1323 (1998); North et al., Obstet Gynecol 83:378–386 (1994); Harrington et al., Br J Obstet Gynecol 104:674–681 (1997). These Doppler abnormalities have been detected in the second trimester of pregnancy usually before the presence of clinical disease. These findings suggest that placental ischemia maybe secondary to decreased blood flow. In turn placental ischemia may lead to widespread dysregulation of placental gene expression with systemic effects such as dysfunction of the vascular endothelium. However, it is still not clear if the reduced uteroplacental blood flow is a cause or effect of poor placentation, which appears to be the critical feature of preeclampsia.

In the mouse placenta the spiral arteries increase in diameter from E10.5–14.5 (Adamson et al., Dev Biol 250: 358–373 (2002)), in order to facilitate an increase in blood flow. The radial arteries in the myometrial region have an intact endothelium, smooth muscle layer and elastic intima. The spiral arteries in the metrial triangle show sparse elastin and an incomplete smooth muscle layer. Further downstream into the decidua no smooth muscle cells are detected surrounding the arteries allowing for vasodilatation and finally endothelium-lined blood spaces are replaced by trophoblast-lined spaces in the ST layer and labyrinth. In the BPH/5 strain we observed that some blood vessels traversing the outer decidua had narrow lumens and persistence of a complete smooth muscle layer. The maternal blood spaces in the inner decidua adjacent to the GC layer were dilated in both BPH/5 mice and C57 controls. These findings suggest the presence of 'unmodified arteries' in the BPH/5 deciduas as has been described in human placentae from women with preeclampsia. Brosens et al., Obstet Gynecol Annu 1:177–191(1972); Zhou et al., J Clin Invest 99:2152–2164 (1997). In preeclampsia, cytotrophoblast invasion is abnormally shallow, resulting in modified spiral arteries in the decidual segments but not in the myometrial segments. Brosens et al., Br J Obstet Gynaecol 84:656–663 (1977); Gerretsen et al., Br J Obstet Gynaecol 88:876–881 (1981). In contrast in normal human pregnancies, the process of extravillous cytotrophoblast invasion extends to the spiral arteries and transforms these vessels into large structureless conduits that can accommodate the vastly increased blood flow to the placenta.

Preeclampsia is associated with defects in placental angiogenesis indicated by failure of human cytotrophoblasts to invade maternal spiral arteries and convert from an epithelial to an endothelial phenotype (pseudovasculogenesis). Zhou et al., J Clin Invest 99:2152–2164(1997). Dysregulation of VEGF family ligands and receptors occurs in severe preeclampsia. Zhou et al., Am J Pathol 160:1405–1423 (2002). In addition, serum free VEGF and placental growth factor (PlGF) levels are reduced while levels of sFLT-1, a VEGF antagonist are increased in women with preeclampsia. Maynard et al., J. Clin. Invest. 111: 649–658 (2003). In the mouse placenta trophoblast giant cells express multiple angiogenic factors critical for maternal and fetal vascular development. Although we were unable to detect a histological abnormality in the giant cell layer, the expression of two genes specific to this layer namely, PL1 and the angiogenic hormone PLF were noted to be significantly reduced. Maximum reduction in PL1 (112fold) and PLF (68fold) was noted at E9.5. This corresponds to the time when peak mRNA and protein expression for both these hormones has been described in the normal mouse placenta. Colosi et al., Mol. Endocrinol 1:767–776 (1987); Linzer et al., Mol Endocrinol 13:837–840 (1999); Linzer et al., Proc. Natl. Acad. Sci. USA 82:4356–4359 (1985). The majority of the soluble angiogenic activity secreted by the midgestation placenta, as measured by an endothelial cell chemotaxis assay, is attributable to PLF. Jackson et al., Science 266:1581–1584 (1994). PLF stimulates endothelial cell migration and neovascularization and plays a role in reorganization and growth of maternal uterine blood vessels towards the developing fetus. Jackson et al., Science 266:1581–1584 (1994). In addition the expression of VEGF was also significantly decreased in BPH/5 placentas throughout gestation. Markedly reduced levels of these two angiogenic hormones early in gestation could also contribute to poor development of the labyrinthine vasculature as seen in our model. Another cause of abnormal placental and decidual vascularization may be attributed to altered expression of placental anti-angiogenic factors, Prp (Bengston et al., Mol Endo 14(12):1934–1943 (2000)), and sFLT-1 (Maynard et al., J. Clin. Invest. 111:649–658 (2003)). Both these genes are expressed in the ST layer, which is markedly reduced in the BPH/5 mouse. Prp, a proliferin antagonist, inhibits excessive migration of maternal blood vessels towards the mouse placenta and prevents endothelial cells in contact with trophoblast from resealing. Linzer et al., Mol Endocrinol 13:837–840 (1999). The reduced ratio of PLF: Prp in BPH/5 placentas indicates an overall decrease in angiogenic activity as early as midgestation compared to C57 mice. Placental expression of the VEGF antagonist s-Flt-1 was unchanged in mid and late gestation. However, we were unable to compute the overall angiogenic effects produced by VEGF/sFlt-1 in our model due to primer differences. It has been reported previously that altering the ratio of VEGF to sFlt-1 can modify the net angiogenic effects in the placenta (He et al., Mol Endo 13:537–545 (1999)) and the glomerular vascular permeability in the kidneys. Sugimoto et al., J Biol Chem. 278(15): 12605–8 (2003). In addition, expression of adrenomedullin, a vasodilator peptide was also significantly decreased at midgestation E9.5 (6fold). Peak expression of adrenomedullin in trophoblast giant cells has been shown from E7–9 with subsequent rapid decline. Yotsumoto et al., Dev Biol 203: 264–275 (1998). Adrenomedullin acts on blood vessels in the mouse decidua and may enhance pooling of maternal blood at the implantation site. In summary, these data suggest that genes involved in the regulation of angiogenesis and blood supply to the developing placenta are markedly dysregulated in the BPH/5 placentas as early as E9.5. Based on the early alteration of placental genes we propose that the placental pathology is the basis for the abnormalities detected in late gestation namely decreased uterine artery blood flow, endothelial dysfunction, hypertension and proteinuria.

The findings of dramatically lower placental weights in BPH/5 compared to C57 mice supports our original observations that both fetal weights and litter sizes were decreased in BPH/5 mice. Davisson et al., Hypertension 39 (part 2):337–42 (2002). Small placentas have also been described in women with severe preeclampsia and IUGR. Redline et al., Hum Pathol 26:594–601 (1995). This reduced size detected in BPH/5 placentas was primarily due to a decrease in the ST layer from mid gestation up to E18.5. Although the exact function of the ST layer is unknown, it is proposed that a subset of these cells differentiate into giant cells. Rossant et al., J Embryol Exp Morphol 62:217–227 (1981); Rossant et al., J Embryol Exp Morphol 39:183–194 (1977); Carney et al., Mol Reprod Dev 34:357–368 (1993). This could explain the markedly decreased expression of PL1 and PLF, which are hormones specific to the giant cell layer. The cells displaying interstitial invasion of the decidua have the characteristic morphology of glycogen trophoblast cells and most likely represent a differentiated subtype of the spongiotrophoblasts. Interestingly, pregnant $p57^{Kip2}-/+$ mice have preeclampsia-like symptoms including hypertension, proteinuria, decreased platelet and anti-thrombin III activity in late gestation. Kanayama et al., Mol. Hum. Reprod. 8:1129–1135 (2002). Since $p57^{kip2}$ is an important regulator of labyrinthine and spongiotrophoblast proliferation in mice (Takahashi et al., Mol Hum Reprod 6:1019–1025 (2000)) it was used to further evaluate these cells in the ST layer. Invasion of $p57^{kip2}$-positive spongiotrophoblasts into the maternal decidua has been demonstrated at E15.5. Georgiades et al., PNAS 98:4522–4527 (2001). However, at this gestational age we found very few $p57^{kip2}$-positive cells in the maternal decidua of BPH/5 mice. Although the exact significance of the decreased $p57^{Kip2}$ expression in our study is unclear it further supports the notion that gene expression and cellular function of the ST layer is impaired.

Although the BPH/5 mouse has several relevant features of preeclampsia, there are some limitations to our mouse model. It represents the clinical syndrome of severe preeclampsia and not the entire spectrum of clinical manifestations as seen in the human disease. The feto-placental abnormalities in this model are supported by the data in the human literature. Women with mild chronic hypertension have a 25% risk of developing superimposed preeclampsia during pregnancy with high rates of preterm delivery, small for gestational age fetuses and perinatal death. Sibai et al., N Engl J Med. 339(10):667–71 (1998). In addition, although the human and mouse placentas are hemochorial we are aware that extrapolations need to be made with some caution since all cell types are not represented physically or functionally in both species.

In summary, the BPH/5 mouse model resembles several clinical and pathological features of severe preeclampsia. We have previously reported that BPH/5 mice spontaneously develop late gestational hypertension, proteinuria, endothelial dysfunction and are associated with increased fetal demise. Davisson et al., Hypertension 39 (part 2):337–42 (2002). In this study we describe early evidence of severe placental morphological abnormalities, downregulation of genes critical for placental angiogenesis and decreased uterine blood flow in BPW/5 mice. These findings provide an understanding of the time course of placental and systemic events in the BPH/5 model and will thereby help to better elucidate the causative agent (s) in the pathophysiology of preeclampsia. We hypothesize that in our mouse model the placenta plays an early and central role in the pathogenesis of preeclampsia.

REFERENCES

Abitbol, M. M., Simplified technique to produce toxemia in the rat: consideration on cause of toxemia. Clin Exp Hyper Hyper Preg B1 (1982), pp. 93–103

Adamson, S L, Yong Lu, Kathie J. Whiteley, Doug Holmyard, Myriam Hemberger, Christine Pfarrer and James C. Cross Interactions between Trophoblast Cells and the Maternal and Fetal Circulation in the Mouse Placenta, 2002 Dev Biol 250, 358–373

Alexander, B T, Bennett, W A, Kahil, R A, Granger, J P. News Phys Sci 16:282–286 (2001).

Baylis, C. Glomerular filtration and volume reguation in gravid animal models. In: Lindheimer, M D; Davison, J M, eds. *Baillieres Clinical Obstetrics and Gynecology* (*vol* 8). London, Ballieres Tindall, 1994, pp 235–264.

Bengston, N. W. and Linzer, D. I. H. (2000) Inhibition of tumor growth by the anti-angiogenic placental hormone, proliferin-related protein. Mol Endo 14(12) 1934–1943.

Brosens, I. A., Robertson, W. B., Dixon, H. G., The role of the spiral arteries in the pathogenesis of preeclampsia. Obstet Gynecol Annu 1972, 1:177–191.

Brosens, I., Dixon, H. G. and Robertson, W. B., Fetal growth retardation and the arteries of the placental bed. Br J Obstet Gynaecol 84 (1977), pp. 656–663.

Butz, G. M., Davisson, R. L., Long-term telemetric measurement of cardiovascular parameters in awake mice: a physiological genomics tool. *Physiol Genomics.* 2001;5:89–97.

Caniggia I., Grisaru-Gravnoski S., Kuliszewski M., Post M., Lye S. J., J Clin Invest 1999;103:1641–1650.

Carney, E., W., Prideaux, V., Lye, S. J. and Rossant, J., Progressive expression of trophoblast-specific genes during formation of mouse trophoblast giant cells in vitro. Mol Reprod Dev 34 (1993), pp. 357–368.

Conrad, K. P., Animal models of pre-eclampsia: do they exist?. Fetal Med Rev 2 (1990), pp. 67–88.

Chambers, J. C., Fusi, L., Malik, I. S., Haskard, D. O., De Swiet, M., Kooner, J. S., Association of maternal endothelial dysfunction with preeclampsia. *JAMA,* 285:1607–1612 (2001).

Chun D., Braga C., Chow C., and Lok L. Clinical observations on some aspects of hydatidiform moles. Obstet Gynaecol Br Commonw 71 (1964), pp. 180–184.

Clark, K. E., Durnwald, M., Austin J. E., A model for studying chronic reduction in uterine blood flow in pregnant sheep. Am J. Physiol. 242:H297–H301 (1982).

Colosi, P., Talamantes, F. and Linzer, D. I. H (1987). Molecular cloning and expression of mouse placental lactogen I complementary deoxyribonucleic acid. Mol. Endocrinol 1, 767–776.

Cross, J. C., Genetic insights into trophoblast differentiation and placental morphogenesis. Semin. Cell Dev. Biol. 11:105–113 (2000).

Croy, B. A., Ashkar, A. A., Minhas, K., and Greenwood J. D., Can murine uterine natural killer cells give insights into the pathogenesis of preeclampsia?. J. Soc. Gynecol. Investig. 7 (2000), pp. 12–20.

Cunningham, F., MacDonald, P. C., Gant, N. F., Leveno, K. J., Gilstrap, L. C., Hankins, G. D., Clark, S. L., Hypertensive disorders of pregnancy. In: Williams Obstetrics. Stamford, Conn.: Appleton & Lange, 1997, p 693–744.

Davisson, R. L., Hoffmann, D. S., Butz, G. M., Aldape, G., Schlager, G., Merrill, D. C., Sethi S., Weiss, R. M., Bates, J. N., Discovery of a spontaneous genetic mouse model of preeclampsia. Hypertension 39 (part 2):337–42 (2002).

Georgiades, P., Watkins, M., Burton, G. J., and Ferguson-Smith, A. C., Roles for genomic imprinting and the zygotic genome in placental development PNAS 2001 98:4522–4527; 2001.

Gerretsen, G., Huisjes, H. J. and Elema, J. D., Phological changes of the spiral arteries in the placental bed in relation to pre-eclampsia and fetal growth retardation. Br J Obstet Gynaecol 88 (1981), pp. 876–881.

Great Britain Department of Health. Why Mothers Die: Report on Confidential Enquiries into Maternal Deaths in the United Kingdom 1994–1996. London:TSO; 1998.

Harrington K., Carpenter R. G., Goldfrad C., Campbell S., Transvaginal ultrasound of the uteroplacental circulation in the early prediction of pre-eclampsia and intrauterine growth retardation. Br J Obstet Gynecol 104:674–681 (1997).

He Y., Smith S. K., Day, K. A., Clark D. E., Licence D. R., and Charnock-Jones D. S., Alternative splicing o vascular endothelial growth factor (VEGF)-R1 (Flt-1) pre-mRNA is important for the regulation of VEGF activity. Mol Endo 13:537–545 (1999).

Hill, J. A., Karimi M., Kutschke, W., Davisson, R. L., Zimmerman, R. L., Zimmerman, K., Wang, Z., Kerber, R. E., Weiss, R. M., Cardiac hypertrophy is not a required compensatory response to short-term pressure overload. Circulation 2000 Jun. 20:101(24):2863–9.

Jackson, D., Volpert, O. V., Bouck, N. and Linzer, D. I. H (1994). Stimulation and inhibition of angiogenesis by placental proliferin and proliferin-related protein, Science 266, 1581–1584.

Kanayama, N., Takahashi, K., Matsuura, T., Sugimura, M., Kobayashi, T., Moniwa, N., Tomita, M., and Nakayama, K., Deficiency in p57Kip2expression induces preeclampsia-like symptoms in mice, Mol. Hum. Reprod. 8:1129–1135 (2002).

Linzer, D. I. H., Fisher, S. J., The placenta and the prolactin family of hormones: regulation of the physiology of pregnancy. Mol Endocrinol 13:837–840 (1999).

Linzer, D. I. H., Lee, S.-J., Ogren, L., Talamantes, F. and Nathans, D (1985). Identification of proliferin mRNA and protein in mouse placenta. Proc. Natl. Acad. Sci. USA 82, 4356–4359.

Losonczy, G. and Mucha I., Potentiation of reduced uteroplacental perfusion pressure hypertension in pregnant rabbits. Hypertension in Preg. 12:475–485 (1993).

MacKay, A. P., Berg, C. J., Hani, A. K., M. D., Pregnancy-Related Mortality From Preeclampsia and Eclampsia. Obstr. Gynecol. 97:533–538 (2001).

Maynard, S. E., Min, J. Y., Merchan, J., Lim, K H, Li, J., Mondal, S., Libermann, T. A., Morgan, J. P., Sellke, F. W., Stillman, I. E., Epstein, F. H., Sukhatme, V. P., and Karumanchi, S. A.,. Excess placental soluble fms-like tyrosine kinase 1 (sFlt1) may contribute to endothelial dysfunction, hypertension, and proteinuria in preeclampsia J. Clin. Invest. 111: 649–658 (2003).

Mires G. J., Williams, F. L., Leslie, J. and Howie, P. W., Assessment of uterine arterial notching as a screening test for adverse pregnancy outcome. Am J Obstet Gynecol 179 (1998), pp. 1317–1323.

Morgan, T, Ward, K. New insights into the genetics of preeclampsia Sem Perinatol. 23:14–23 (1999).

National High Blood Pressure Education Program Working Group Report on High Blood Pressure in Pregnancy. Am J Obstet Gynecol. 1990;163:1691–1712.

North R. A., Ferrier C., Long D., Townend K., Kincaid-Smith P., Uterine artery Doppler flow velocity waveforms in the second trimester for the prediction of preeclampsia and fetal growth retardation. Obstet Gynecol 1994; 83:378–386.

O'Donnell, M. P., Michels, L., Kasike, B., Adriamycin-induced chronic proteinuria: A structural and functional study. J Lab Clin Med. 106:62–67 (1985).

Piering, W. F., Garancis, J. G, Becker, C. G., Beres, J. A. and Lemann, J., Preeclampsia related to a functioning extrauterine placenta, report of a case and 25-year follow-up. Am J Kid Dis 21 (1993), pp. 310–313.

Podjarny, E., Baylis, C., Losonczy G., Animal models of preeclampsia. Sem. Perinatol. 1999;23:2–12.

Redman C. W. G., Sargent I. L. Placental debris, oxidative stress and preeclampsia. Placenta 2000, 21, 597–602.

Redline R. W., Patterson, P., Hum Pathol 1995;26:594–601

Reiter, T., Brown, M. A., Whitworth, J. A., Hypertension in pregnancy: the incidence of underlying renal disease and essential hypertension. *Am J Kid Dis.* 1994;24:883–887.

Roberts, J. M., Taylor, R. N. and Goldfien, A., Clinical and biochemical evidence of endothelial cell dysfunction in the pregnancy syndrome preeclampsia. Am J Hypertens 4 (1991), pp. 700–708.

Roberts, J. M., Taylor, R. N., Musci, T. J., Rodgers, G. M., Hubel, C. A. & McLaughlin, M. K. (1989) Preeclampsia: An endothelial cell disorder. Am. J. Obstet. Gynecol. 161: 1200–1204.

Roberts, J. M. & Hubel, C. A. (1999) Is oxidative stress the link in the two-stage model of pre-eclampsia? Lancet 354: 788–789.

Roberts, J. M., Cooper, D. W., Pathogenesis and genetics of preeclampsia. *Lancet.* 2001;357:53–56.

Rossant, J. and Ofer L., Properties of extra-embryonic ectoderm isolated from postimplantation mouse embryos. J Embryol Exp Morphol 39 (1977), pp. 183–194.

Rossant, J., Cross J. C., Placental Development: lessons from mouse mutants. (2001) Nature Reviews Genetics 2, 538–548.

Rossant, J. and Tamura-Lis, W., Effect of culture conditions on diploid to giant-cell transformation in postimplantation mouse trophoblast. J Embryol Exp Morphol 62 (1981), pp.217–227.

Schlager, G., Lester, J. W. and Carrithers, J. A., Characteristics of the inbred hypertensive mouse strains. FASEB J. 3:A1315 (1989).

Schlager, G. Genetic hypertension in mice. In: Ganten, D, DeJong, W, eds. Handbook of Hypertension. Amsterdam, Netherlands: Elsevier; 1994:158–172.

Sibai, B. M., Lindheimer M., Hauth J., Caritis S., VanDorsten P., Klebanoff M., MacPherson C., Landon M., Miodovnik M., Paul R., Meis P., Dombrowski M., Risk factors for preeclampsia, abruptio placentae, and adverse neonatal outcomes among women with chronic hypertension. National Institute of Child Health and Human Development Network of Maternal-Fetal Medicine Units N Engl J Med. 339(10):667–71 (1988).

Sugimoto, H., Hamano, Y., Charytan, D., Cosgrove, D., Kieran, M., Sudhakar, A., Kalluri, R., Neutralization of circulating vascular endothelial growth factor (VEGF) by anti-VEGF antibodies and soluble VEGF receptor 1 (sFlt-1) induces proteinuria. J Biol Chem. 278(15):12605–8 (2003).

Takeda, T. Experimental study on the blood pressure of pregnant hypertensive rats. Jap Circ J. 28:49–54 (1964).

Takimoto, E., Ishida, J., Sugiyama, F., Horiguchi, H., Murakami, K., Fukamizu, A., Hypertension induced in pregnant mice by placental renin and maternal angiotensinogen. Science. 274:995–998 (1996).

Takahashi, K., Kobayashi T., Kanayama, N., p57Kip2regulates the proper development of labyrinthine and spongiotrophoblasts Mol Hum Reprod 2000 6: 1019–1025.

Taylor, R. N., de Groot, C. J., Cho, Y. K., Lim, K. H., Circulating factors as markers and mediators of endothelial cell function in preeclampsia. Sem Reprod Endocrinol. 1998;16:17–31.

Ventura S J M J, Curtin S. C., Menacker F., Hamilton B. E., Births: final data for 1999. National Vital Statistics Reports. 2001:49.

Walker J. J., Pre-eclampsia. Lancet 2000, 356:1260–1265.

Yallampalli, C., Garfield, R. E., Inhibition of nitric oxide synthesis in rats during pregnancy produces signs similar to preeclampsia. Am J Obstet Gynecol. 169:1316–1320 (1993).

Yotsumoto, S., Shimada, T., Cui, C Y., Nakashima, H., Fujiwara H, Ko, M. S. H. Expression of Adrenomedullin, a Hypotensive Peptide, in the Trophoblast Giant Cells at the Embryo Implantation Site in Mouse, (1998) Dev Biol 203, 264–275.

Zhou, Y., Damsky, C. H. and Fisher, S. J., Preeclampsia is associated with failure of human cytotrophoblasts to mimic a vascular adhesion phenotype. One cause of defective endovascular invasion in this syndrome?. J Clin Invest 99 (1997), pp. 2152–2164.

Zhou, Y., McMaster, M., Woo, K., Janatpour, M., Perry, J., Karpanen, T., Alitalo, K., Damsky, C., and Fisher, S. J., Vascular Endothelial Growth Factor Ligands and Receptors That Regulate Human Cytotrophoblast Survival Are Dysregulated in Severe Preeclampsia and Hemolysis, Elevated Liver Enzymes, and Low Platelets Syndrome. Am J Pathol 160:1405–1423 (2002).

What is claimed is:

1. A method for screening for compounds useful for the treatment or amelioration of preeclampsia and/or the symptoms thereof comprising:
   inducing preeclampsia in a BPH/5 mouse;
   administering a test compound to the mouse; and
   monitoring the mouse for amelioration or elimination of preeclampsia or its symptoms, wherein amelioration or elimination of preeclampsia or its symptoms in the mouse indicates usefulness of the compound for the treatment of preeclampsia.

2. The method of clam 1, wherein preeclampsia is induced by mating the BPH/5 mouse with another mouse such that the BPH/5 mouse becomes pregnant.

3. A method for screening for compounds useful for the treatment of preeclampsia comprising:
   mating a female BPH/5 mouse with another mouse wherein the BPH/5 mouse becomes pregnant and exhibits preeclampsia;
   administering a test compound to the pregnant BPH/5 mouse; and
   monitoring the pregnant BPH/5 mouse for amelioration or elimination of preeclampsia, wherein amelioration or elimination of preeclampsia in the pregnant BPH/5 mouse indicates usefulness of the compound for the treatment of preeclampsia.

4. A method of screening a candidate compound for alleviating preeclampsia, said method comprising:
   inducing preeclampsia in a BPH5 mouse by impregnating said mouse;
   administering a compound to said BPH/5 mouse; and
   comparing the induced preeclampsia condition in said BPH/5 mouse with the induced preeclampsia condition in a control BPH/5 mouse that did not receive said candidate compound, wherein an amelioration or elimination in the preeclampsia condition of the treated BPH/5 mouse is indicative of the alleviating activity of said candidate compound.

5. A method of screening a candidate compound for the prevention of preeclampsia, said method comprising:
   administering a compound to a BPH/5 mouse;
   inducing pregnancy in said mouse; and
   comparing the pregnant condition in said mouse with said candidate agent with a pregnant control BPH/5 mouse exhibiting preeclampsia, wherein the prevention or reduction of the affects of the preeclampsia condition of the treated mouse is indicative of the alleviating activity of said candidate compound.

* * * * *